(12) United States Patent
Bouquet

(10) Patent No.: US 11,931,012 B2
(45) Date of Patent: Mar. 19, 2024

(54) VAGINAL SPECULUM AND CERVICAL SCREENING KIT

(71) Applicant: Viospex, Parker, CO (US)

(72) Inventor: Jean Bouquet, Parker, CO (US)

(73) Assignee: Viospex, Parker, CO (US)

( * ) Notice: Subject to any disclaimer, the term of this patent is extended or adjusted under 35 U.S.C. 154(b) by 0 days.

(21) Appl. No.: 16/058,128

(22) Filed: Aug. 8, 2018

(65) Prior Publication Data

US 2018/0344144 A1    Dec. 6, 2018

Related U.S. Application Data

(63) Continuation-in-part of application No. 16/008,338, filed on Jun. 14, 2018, now abandoned, which is a continuation of application No. 15/783,690, filed on Oct. 13, 2017, now abandoned, which is a continuation of application No. 14/342,521, filed as (Continued)

(51) Int. Cl.
| | |
|---|---|
| *A61B 1/303* | (2006.01) |
| *A61B 1/00* | (2006.01) |
| *A61B 1/06* | (2006.01) |
| *A61B 1/07* | (2006.01) |
| *A61B 1/32* | (2006.01) |
| *A61M 29/00* | (2006.01) |
| *A61B 10/00* | (2006.01) |

(52) U.S. Cl.
CPC .......... *A61B 1/303* (2013.01); *A61B 1/00126* (2013.01); *A61B 1/0669* (2013.01); *A61B 1/07* (2013.01); *A61B 1/32* (2013.01); *A61B 2010/0074* (2013.01); *A61M 29/00* (2013.01)

(58) Field of Classification Search
CPC .......... A61B 1/303; A61B 1/32; A61M 29/00
See application file for complete search history.

(56) References Cited

U.S. PATENT DOCUMENTS

| 380,745 A | * | 4/1888 | Molesworth | ............. | A61B 1/32 |
| | | | | | 600/224 |
| 400,589 A | * | 4/1889 | Chamberlin | ............. | A61B 1/32 |
| | | | | | 600/203 |

(Continued)

FOREIGN PATENT DOCUMENTS

| FR | 2698778 A1 | * | 6/1994 | ............... | A61B 1/32 |
| WO | 97-24975 | | 7/1997 | | |
| WO | WO-0121060 A1 | * | 3/2001 | ............... | A61B 1/32 |

*Primary Examiner* — Matthew J Lawson
(74) *Attorney, Agent, or Firm* — Davis Graham & Stubbs LLP

(57) ABSTRACT

A vaginal speculum, conical in shape made out of clear plastic resin or metal that when closed can easily and gently be inserted into the introitus (vaginal opening). In certain embodiments, a dilator is used to introduce and/or expand the speculum. Various mechanisms are disclosed for dilating the speculum, after it has been inserted, so as to allow inspection of the patient's cervix. Such dilation can be affected relative to multiple axes, or even in substantially continuous, radial fashion about the periphery of the speculum, for improved visualization. In addition, this speculum has a handle that is oriented such that a vaginal exam can be performed on a standard exam table. The handle also includes a receptacle that receives a standard pen light. A self-contained kit is also provided to facilitate cervical examinations and treatment.

14 Claims, 24 Drawing Sheets

Related U.S. Application Data application No. PCT/US2012/053464 on Aug. 31, 2012, now abandoned, which is a continuation-in-part of application No. 13/224,421, filed on Sep. 2, 2011, now Pat. No. 8,460,187.

(56) References Cited

U.S. PATENT DOCUMENTS

| | | | |
|---|---|---|---|
| 5,174,278 | A | 12/1992 | Babkow |
| 5,377,667 | A | 1/1995 | Patton et al. |
| 5,505,690 | A | 4/1996 | Patton et al. |
| 5,795,289 | A | 8/1998 | Wyttenbach |
| 6,004,265 | A | 12/1999 | Hsu et al. |
| 6,036,638 | A | 3/2000 | Nwawka |
| 6,280,379 | B1 | 8/2001 | Resnick |
| 6,287,251 | B1 * | 9/2001 | Tan ............... A61B 1/32 600/224 |
| 6,364,832 | B1 | 4/2002 | Propp |
| 6,432,048 | B1 | 8/2002 | Francois |
| 7,060,029 | B1 | 6/2006 | Hajianpour |
| 7,063,664 | B2 | 6/2006 | Mohajer |
| 7,374,534 | B2 * | 5/2008 | Dalton ............ A61B 17/3439 600/222 |
| 8,795,326 | B2 * | 8/2014 | Richard ........... A61B 17/3423 600/206 |
| 9,050,048 | B2 * | 6/2015 | Nadershahi ............. A61B 1/32 |
| 9,848,864 | B2 * | 12/2017 | Lauchner ............... A61B 90/30 |
| 2003/0069477 | A1 | 4/2003 | Raisman et al. |
| 2005/0021080 | A1 | 1/2005 | Feuer et al. |
| 2005/0192482 | A1 | 9/2005 | Carpenter et al. |
| 2005/0234497 | A1 * | 10/2005 | Hung ............... A61M 29/00 606/191 |
| 2006/0079924 | A1 | 4/2006 | Sanders et al. |
| 2007/0038216 | A1 * | 2/2007 | Hamada ............. A61B 17/02 606/53 |
| 2007/0198045 | A1 * | 8/2007 | Morton ........... A61B 17/3439 606/191 |
| 2007/0219416 | A1 * | 9/2007 | Perez-Cruet ........ A61B 17/02 600/219 |
| 2008/0275306 | A1 * | 11/2008 | Rebuffat ................ A61B 1/31 600/184 |
| 2011/0040234 | A1 * | 2/2011 | Chaffringeon ...... A61F 13/266 604/15 |
| 2011/0082375 | A1 * | 4/2011 | Sakhel ................ A61B 1/303 600/462 |
| 2014/0114136 | A1 * | 4/2014 | Ellman ............. A61B 17/025 600/214 |
| 2017/0265892 | A1 * | 9/2017 | Winegar ......... A61B 17/3421 |
| 2017/0303903 | A1 * | 10/2017 | de Koning ........... A61B 1/303 |

* cited by examiner

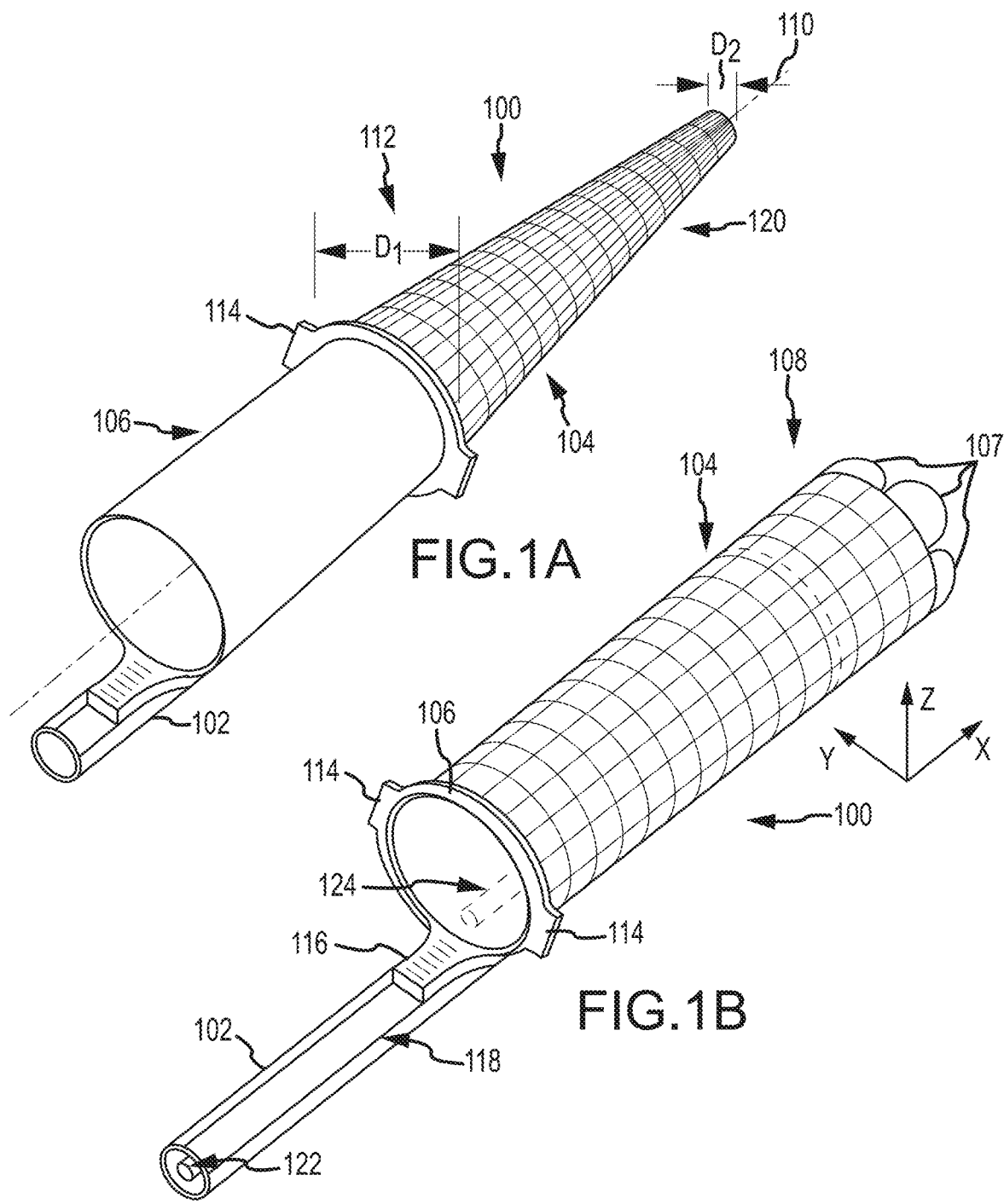

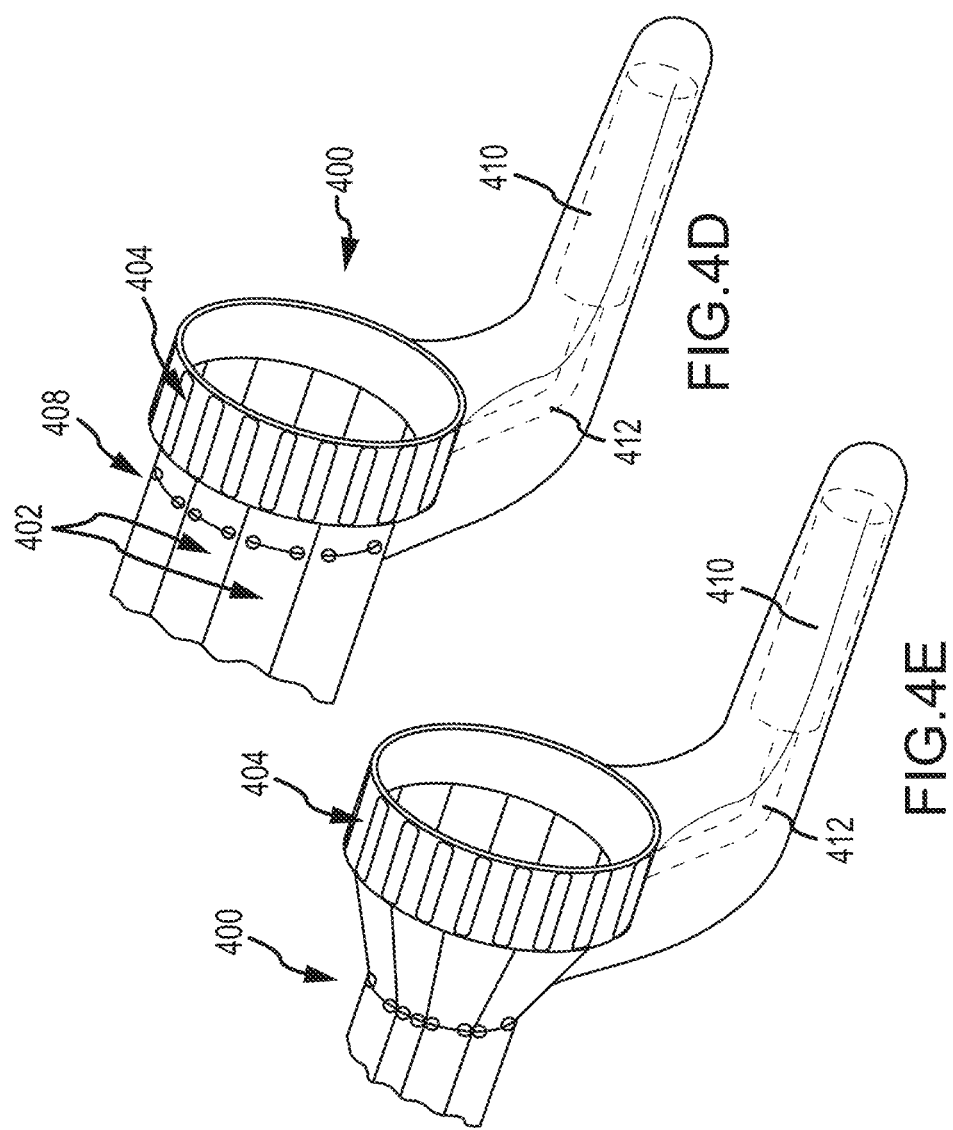

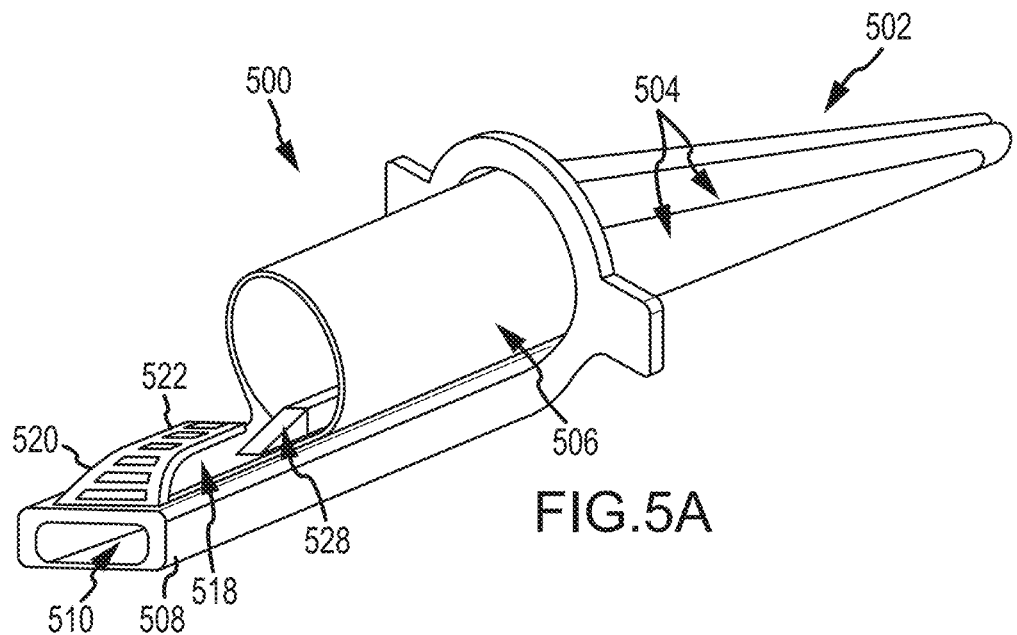
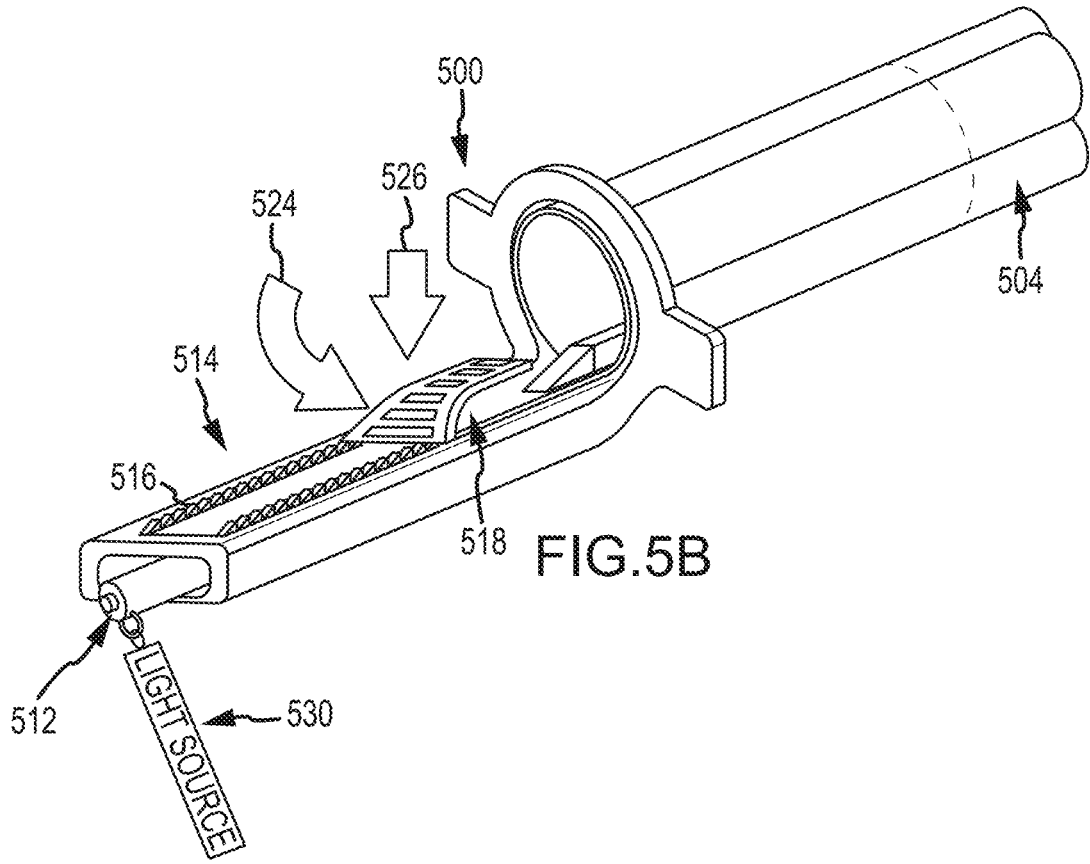

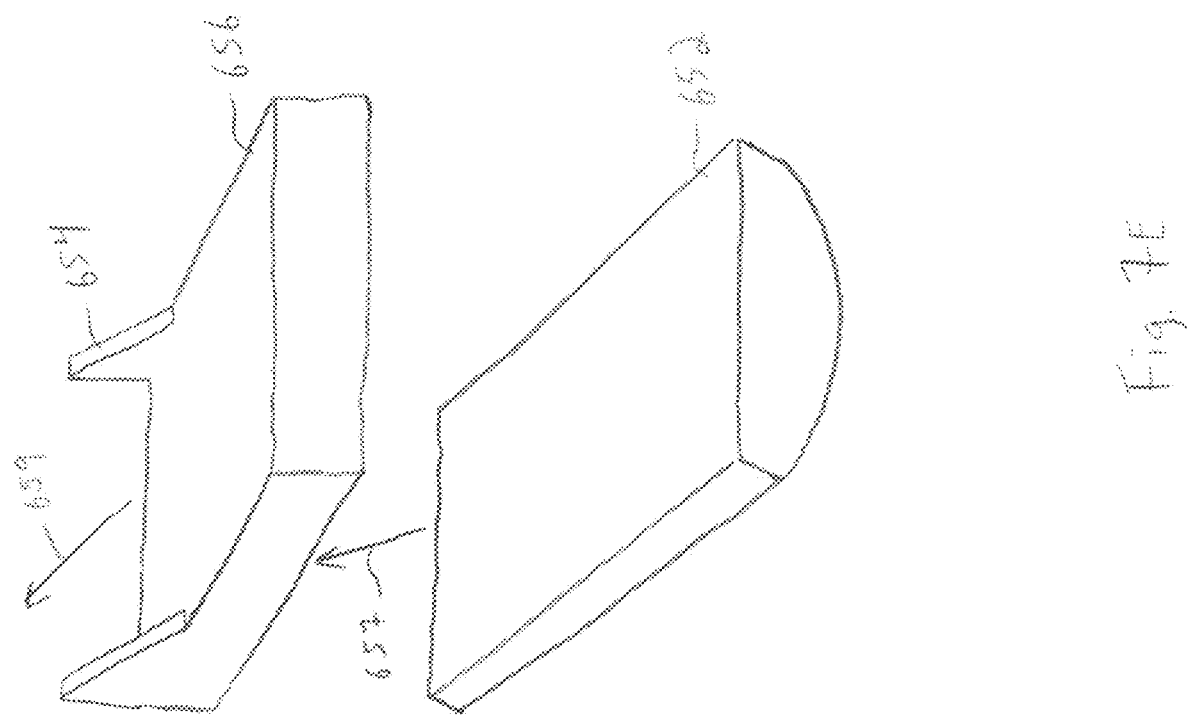

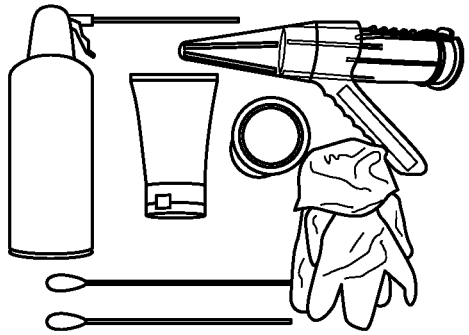
1. KIT
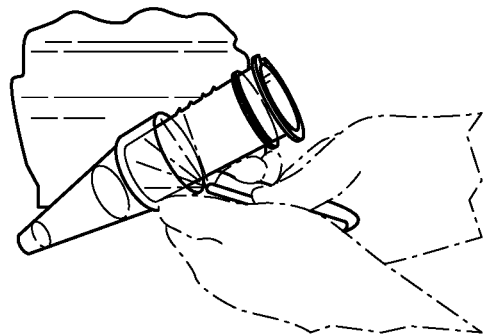
2. SNAP PENLIGHT INTO HANDLE AND TURN ON
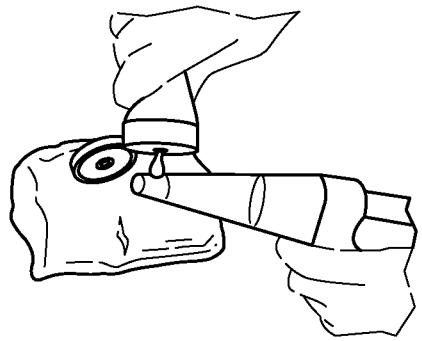
3. APPLY LUBRICANT LIBERALLY TO SPECULUM
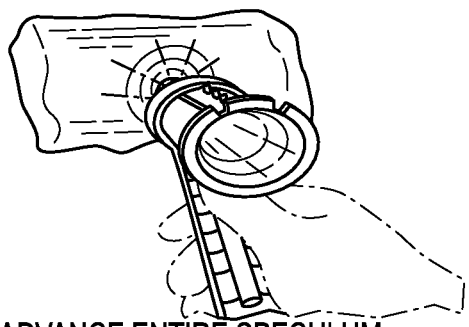
4. ADVANCE ENTIRE SPECULUM TO RESISTANCE
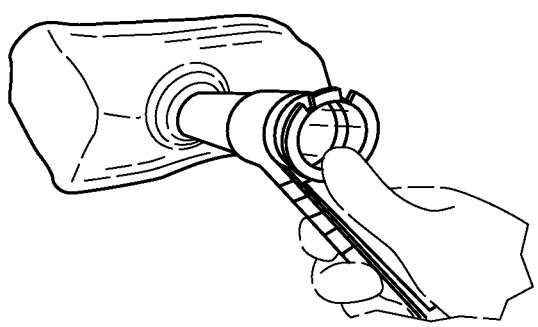
5. ADVANCE DILATOR TO DESIRED OPENING
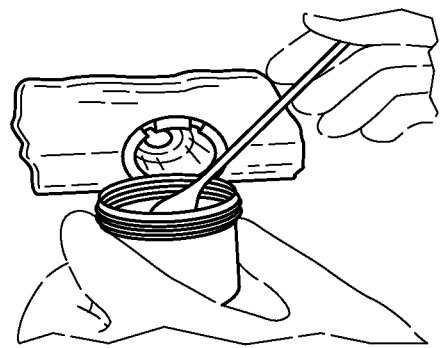
6. APPLY VINEGAR (ACETIC ACID 5%) TO CERVIX
FIG.9A

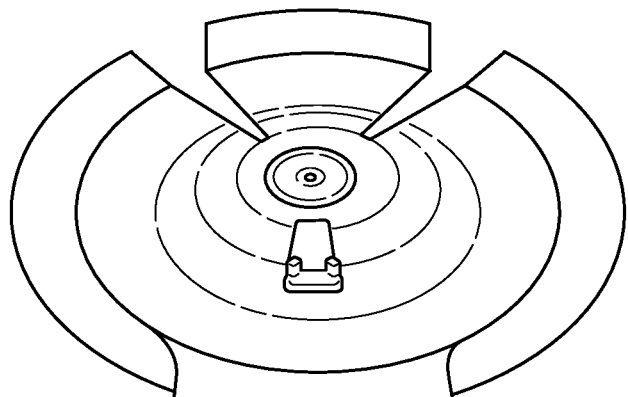
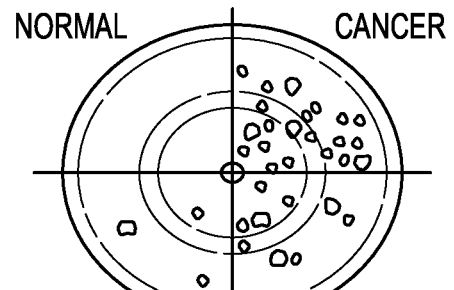
7. AFTER 45 SECONDS, OBSERVE CERVIX FOR ANY ACETOWHITE LESIONS
8. EXAMPLES OF PRE-CANCER/CANCER OF CERVIX
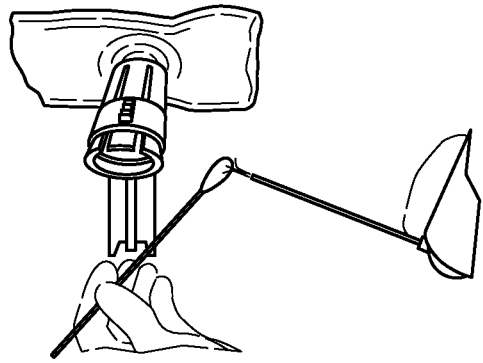
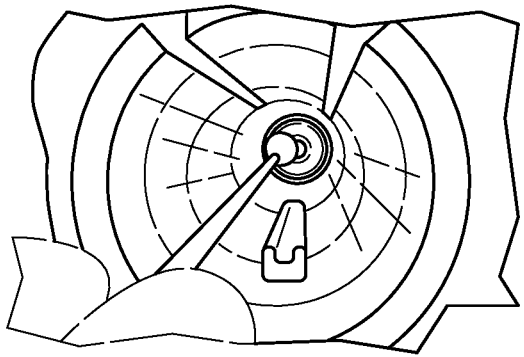
9. TURN CRYO BOTTLE UPSIDE DOWN AND SPRAY APPLICATOR FOR 10 SECONDS
10. APPLY TO WHITE LESIONS (IF PRESENT) FOR 45 SECONDS
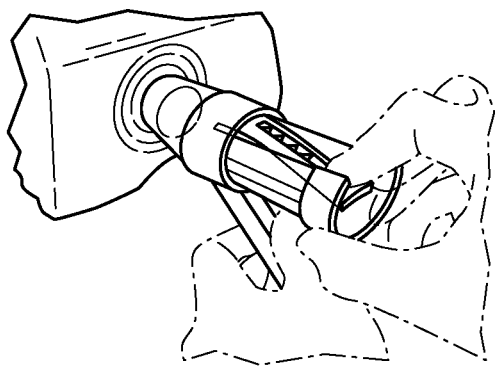
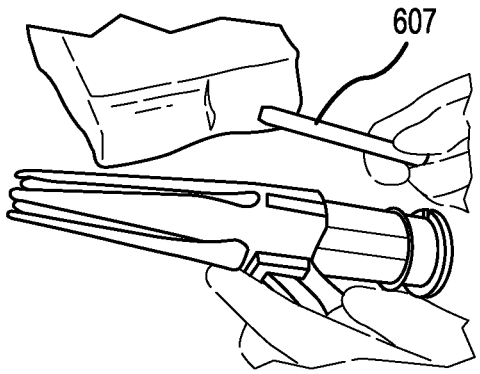
11. PUSH DOWN ON RELEASE AND PULL DILATOR OUT
12. DISPOSE OF SPECULUM. SAVE PENLIGHT
FIG.9B

VAGINAL SPECULUM AND CERVICAL SCREENING KIT

CROSS-REFERENCE TO RELATED APPLICATIONS

This application is a continuation-in-part of U.S. application Ser. No. 16/008,338, entitled, "VAGINAL SPECULUM," filed on Jun. 14, 2018, which is a continuation of U.S. application Ser. No. 15/783,690, entitled, "VAGINAL SPECULUM," filed on Oct. 13, 2017, which is a continuation of U.S. application Ser. No. 14/342,521, entitled, "VAGINAL SPECULUM," filed on Aug. 31, 2012, which is a 371-national stage entry of PCT Application No. PCT/US2012/053464, entitled, "IMPROVED VAGINAL SPECULUM," filed on Aug. 31, 2012, which is a continuation-in-part of U.S. application Ser. No. 13/224,421, entitled, "VAGINAL SPECULUM," filed on Sep. 2, 2011. The contents of the above-noted applications are incorporated by reference herein as if set forth in full and priority to these applications is claimed to the full extent allowable under U.S. law and regulations.

FIELD OF THE INVENTION

The present invention relates to vaginal specula and, in particular, to a radially expanding speculum that improves visualization of the cervix and thereby enhances cervical analysis and procedures. A kit is also disclosed to enable convenient and cost-effective cervical screening and treatment for underserved populations.

BACKGROUND

Vaginal specula are used to dilate the vagina and visualize the uterine cervix to screen and treat for cancerous and benign lesions of the cervix. Generally, existing vaginal specula are two-bladed including a stationary blade (relative to the speculum handle) and a pivoting blade. Some designs allow the pivot point to move linearly away from the stationary blades. Nonetheless, the moveable blade is substantially limited to moving away from and back towards the stationary blade in relation to one axis.

There are several drawbacks to existing speculum designs. The most important of these is the potential failure to fully visualize the cervix which could lead to failure to diagnose cervical cancer—a life threatening condition. In some women, with the two-bladed speculum, the vaginal walls collapse between the two-blades and obscure the view of the cervix. The current two-bladed design has relatively large blades that are difficult to introduce into the vagina of an apprehensive patient. In addition the current speculum also does not take into account the variation in patient anatomy. The uterine cervix typically sits at a 90° angle to the vagina. The two-bladed speculum, as designed, opens asymmetrically. This may cause excessive dilation in certain parts of the vagina thus causing discomfort to the patient.

Moreover, when closing and removing the two-bladed speculum, there are two "pinch points" along the length of the blade members, which can cause patient discomfort upon closing of the blades in preparation for withdrawal. In addition, the current handles on vaginal speculums are generally oriented at 90 degrees relative to the blades necessitating a specialized gynecologic table with stirrups. Certain existing specula also require a halogen light source that is costly and requires AC/DC current. Lastly, the current specula on the market when opened create a very disconcerting clicking sound.

SUMMARY

The present invention provides a new and unique design for a vaginal speculum that reduces or eliminates these existing drawbacks. The ideal speculum, in accordance with the present invention, would be comfortable and non-threatening for the patient, consistently accurate at visualizing the cervix, universal for all body types and anatomy, simple and easy to use for the clinician, and cost effective to manufacture and use on an ongoing basis.

In accordance with one aspect of the present invention, a vaginal speculum is provided that expands in more than one dimension. As noted above, a common type of speculum on the market today expands substantially only in relation to a single dimension. That is, the conventional speculum has two-blades, one of which pivots about an axis so that the associated blade moves on an arcuate path away from or towards the stationary blade. Although the moveable blade and its pivot point may also be moved linearly towards or away from the stationary blade, expansion of the speculum is still substantially limited to a single axis transverse to the longitudinal axis of the blades. This has a number of disadvantages, as described above, including that the vaginal walls of some patients can collapse between the blades impairing visualization of the procedure site.

The inventive speculum in accordance with the present aspect of the invention includes a handle, a petal assembly for separating and retaining the vaginal walls of a patient and a dilation actuator. The petal assembly has a proximal end portion near the handle and a distal end portion remote from the handle and is movable between a contracted configuration, wherein the distal end portion has a reduced circumference, and a dilated configuration wherein the distal end portion is expanded for improved visualization of the cervix. The dilation actuator is operative to expand the distal end portion of the petal assembly in relation to at least a first axis and a second axis transverse to the first axis.

Unlike conventional specula that have a stationary blade (fixed in relation to the handle) and a moveable blade, the inventive speculum may include multiple (two or more) moveable petals. In one embodiment, the speculum has three or more petals, each of which moves outward from a central axis of the dilation assembly. In some embodiments the petals move radially outward whereas, in other embodiments, the petals expand radially outwardly while concomitantly traveling circumferentially in relation to the central axis. Such movement may be actuated by a dilator which is inserted into a hollow interior of the dilation assembly, and withdrawn therefrom, so as to move between the expanded and contracted configurations. The dilator may be moved into and out of the dilation assembly in linear fashion or by operation of a screw mechanism. The speculum may also include a light source receptacle assembly for receiving a light source so that light can be transmitted through the dilation assembly to a procedure site.

In accordance with another aspect of the present invention, a method for using a vaginal speculum is provided. The method includes the steps of: introducing a petal assembly of a speculum into the introitus of a patient; operating a dilation actuator to expand the petal assembly with respect to a first axis and with respect to second axis transverse to the first axis; upon concluding a medical procedure, operating the dilation actuator to contract the petal assembly to a contracted configuration; and withdrawing the petal assembly from the introitus of the patient. The step of expanding the petal assembly may involve, for example, advancing a dilator into a hollow interior of the petal assembly from a proximate end of the petal assembly so as to force the dilation assembly into the expanded configuration. The process may further involve operating a light source mounted in a handle of the speculum to transmit light through the petal assembly so as to illuminate the procedure site.

In accordance with another aspect of the present invention, a speculum is provided with an angled or horizontal handle. Conventional specula typically have an upright handle which, among other things, may be difficult to use when a gynecological examination table is not available. The inventive speculum includes a handle for gripping by a user and a petal assembly connected to the handle where the handle has a longitudinal handle axis disposed at an angle of no more than 75° in relation to a viewing axis of the petal assembly. For example, the handle may be oriented substantially parallel to the viewing axis but offset from the viewing axis by offset structure interconnecting the handle to the petal assembly. Alternatively, the handle may be angled relative to the petal assembly for example at an angle between 25°-75° or, more preferably, between 40°-60°. Such a handle configuration facilitates use where an examination table is not available as noted above and further facilitates access to a dilation mechanism.

In accordance with yet another aspect of the present invention, a speculum is provided with a narrow front end in the contracted configuration. The speculum includes a handle and a petal assembly that is movable between a dilated configuration and a contracted configuration. In the contracted configuration, a front end portion of the petal assembly that includes all of the petals has a maximum dimension of no more than 0.75 inches. In one embodiment, the petals curve inwardly for about the last 0.25 inches adjacent to the forwardmost end of the speculum. In that embodiment, the cross-section of the petal assembly is generally circular and has a diameter at the start of the inwardly curved section of the petals of about 0.5 inches. When the speculum is in a dilated configuration the maximum dimension of the front end portion of the petal assembly, measured relative to the same axis used for the maximum dimension in the contracted configuration, is at least twice the maximum dimension in the contracted configuration and, more preferably, at least about three times the dimension in the contracted configuration. In the embodiment noted above, the front end portion has a diameter of at least about 1.5 inches in the dilated configuration. It will be appreciated that the reduced dimension front end facilitates insertion of the speculum into the patient, increases patient comfort, and facilitates screening of young or small patients.

In accordance with a still further aspect of the present invention, a dilator that advances into the petal assembly is utilized to dilate the petal assembly. The dilator includes an elongate hollow structure and may be provided in the shape of a cylinder or a tapered tube. The dilator can be advanced and retracted by any suitable mechanism and may move linearly or in a helical screwing motion. In addition, a ratcheting mechanism may be provided to allow the dilator to be maintained in any of a number of discrete positions. Among other things, the dilator inhibits collapsing of the vaginal walls into the interior of the petal assembly which could inhibit viewing and access to the cervix as well as potentially result in pinching.

In accordance with another aspect of the present invention, a speculum is provided with multiple moving petals. As noted above, conventional duckbill specula generally include a stationary blade and a movable blade. The inventive speculum includes at least two petals, each of which is movable in relation to the speculum handle. In certain implementations, the speculum includes more than two petals, each of which moves in a different direction relative to the speculum handle. For example, the petals may allow for expansion of the petal assembly relative to first and second transverse axes. It will be appreciated that, even in the case of two movable petals, improved viewing and access to the cervix may be provided. Viewing and access is further enhanced by providing more than two petals that expand relative to multiple axes.

In accordance with a further aspect of the present invention, a speculum is provided that can employ a conventional penlight as a light source. The speculum includes a handle that has an exposed surface for direct access by a user. A light source receptacle is formed on the exposed surface of the handle for receiving the light source. The receptacle is preferably dimensioned to receive inexpensive, off-the-shelf penlights. In this regard, penlights often have a cylindrical shape with a fairly standard diameter related to use of AAA battery as a power source. Accordingly, the width of the receptacle may be about 0.4-0.6 inches, preferably with some give to accommodate variability of commercial penlights. Moreover, the exposed surface receptacle allows for insertion of the light source by sliding along the length of the channel or inserting the light source transverse to the longitudinal axis of the receptacle. The exposed surface receptacle also accommodates use of light sources with an on-off switch on an end surface or a side surface of the light source. The speculum thus allows for use of a low cost penlight and is not limited to use of expensive custom light sources as has sometimes been the case in the past, thereby reducing health care costs and potentially expanding access to cervical examination and treatment.

In accordance with a still further aspect of the present invention, a cervical screening and treatment kit is provided. The kit may include a disposable plastic speculum, surgical gloves, a lubricant container, a visualization agent container, an applicator for the visualization agent, and cervical screening instructions. These components may be placed into one or more kit containers. For example, single use components may be provided in one container and other components deemed suitable for reuse may be provided in another container. The container or containers may then be sealed for distribution. In one implementation, the kit may further include a compressed gas container that can be used for cryoablation of cervical lesions. The kit provides an inexpensive, self-contained unit for cervical screening and treatment. Such a kit can greatly expand access to cervical screening and treatment with the potential to save many lives, particularly in underserved regions.

It will be appreciated that, among other things, the invention encompasses specula, methods for making and using the specula, cervical screening and treatment kits including the inventive speculum and methods for making and using the cervical screening and treatment kits.

BRIEF DESCRIPTION OF THE DRAWINGS

For a more complete understanding of the present invention, and further advantages thereof, reference is now made to the following detailed description taken in conjunction with the drawings in which:

FIGS. 1A and 1B show perspective views of a vaginal speculum, constructed in accordance with the present invention, in a contracted (closed) and an expanded (open) configuration, respectively;

FIGS. 4D-4E show perspective views of a portion of the speculum of FIG. 4A in the open and closed configurations, respectively;

FIGS. 5A-5B, are perspective views of a speculum, in accordance with another embodiment of the present invention, in closed and open configurations, respectively;

FIGS. 5D-5F are side views of distal end petal portions of the speculum of FIGS. 5A-5B in the closed and open configurations, respectively;

FIG. 7E is an exploded perspective view of certain components of the speculum of FIG. 6A;

FIGS. 9A-9B show instructions that may be included in a screening and treatment kit including the speculum of FIG. 6A.

DETAILED DESCRIPTION

Figure 2A:
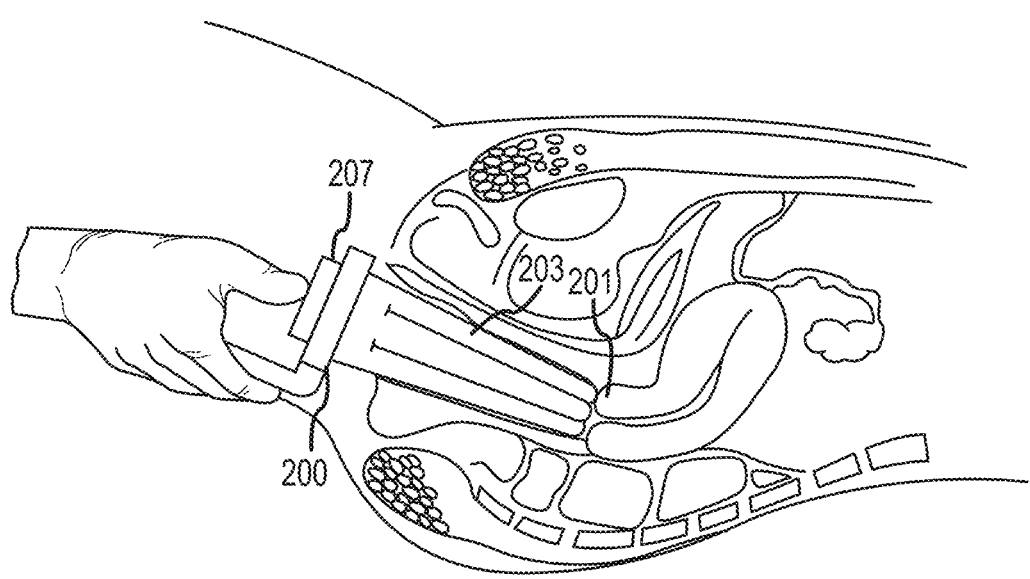
FIGS. 2A and 2B illustrate a vaginal speculum in accordance with the present invention in contracted and expanded configurations, respectively, where the speculum in shown inserted into the introitus of a patient and certain physiology of the patient is depicted for purposes of illustration.

In the following description, the invention is set forth with respect certain specific embodiments of vaginal specula. While these embodiments illustrate the principles of the present invention, it is anticipated that further embodiments of the invention are possible and will be apparent to those skilled in the art upon consideration of the present disclosure. Accordingly, the invention is not limited to the embodiments as set forth herein.

FIGS. 1A and B illustrate perspective views of a speculum 100 in accordance with the present invention. Specifically, FIG. 1A illustrates the speculum 100 in contracted or closed configuration and FIG. 1B illustrates the speculum 100 in a dilated or open configuration. The speculum 100 includes a handle 102 for gripping by a physician or other user, a petal assembly 104 for dilating and retaining the vaginal walls of the patient so as to facilitate visual inspection of the uterine walls and cervix as well as associated medical procedures, and a dilator 106 for use in introducing the petal assembly 104 into the patient and for forcing the petal assembly 104 to the expanded configuration as shown in FIG. 1B. Withdrawing the dilator 106 from the petal assembly 104 allows the petal assembly 104 to return to the contracted configuration as shown in FIG. 1A.

The illustrated petal assembly 104 includes a number of petals 107. As will described in more detail below, at the distal end 108 of the petal assembly 104, remote from the handle 102, the petals 107 can spread apart from one another so as to define the dilated configuration and can come back together in order to define the contracted configuration. The petal assembly 104 preferably includes at least three petals 107 to allow expansion with respect to at least two axes or two dimensions, e.g., the Y and Z dimensions as shown in FIGS. 1A and 1B where the X, Y and Z axes are mutually orthogonal and the X axis is aligned with the longitudinal axis 110 of the petal assembly 104. The illustrated petal assembly 104 includes four petals 107 each of which extends about approximately one quarter or 90° of the periphery of the petal assembly 104 at the distal end 108 in the contracted configuration. The petals 107 may alternatively overlap or remain somewhat separated (e.g., to avoid pinching) in the contracted configuration.

The petal assembly 104 has a generally hollow, truncated conical or bullet-shaped configuration. In the contracted configuration as shown in FIG. 1A, the petal assembly 104 has a diameter, $D_1$, at the proximal end 112, thereof, adjacent the handle 102 of about two inches and a diameter, $D_2$, at the distal end thereof about 0.75 inches. In the expanded configuration as shown in FIG. 1B, the diameter $D_2$ is, for example, about 1.5 inches. The illustrated petal assembly 104 further includes finger grips 114 that may be gripped by the physician or other user to facilitate insertion of the dilator 106 as will be described in more detail below. In the illustrated embodiment, as in the embodiments described below, the petal assembly 104 as well as the handle 102 and/or dilator 106 may be formed from a clear plastic resin, other plastic or metal. In this regard, plastic or resin materials allow for low cost construction as may be desired for single use disposable applications. The speculum 100 may be constructed from metal materials to allow for sterilization and reused if desired. In the illustrated embodiment, the petal assembly 104 is formed from a clear plastic resin.

For example, the body of the petal assembly 104 may be constructed by obtaining or molding the plastic resin in generally cylinderal or conical shape. The plastic resin can then be cut or slit from the distal end toward the proximate end 112 to define the petals 107. Alternatively, the petals 107 may be formed by appropriate molding. In any event, the petals 107 in the illustrated embodiment do not extend the full length of the petal assembly 104. Rather, the petals 107 come together at a location near the proximal end 112 to form a continuous cylinderal side wall. In this manner, the petals 107 flex outwardly to the expanded configuration when the dilator 106 is advanced into the hollow interior of petal assembly 104 from the proximal end 112. When the dilator is withdrawn from the hollow interior of the petal assembly 104, the petals 107 collapse to the contracted configuration, e.g., due to material memory of the clear plastic resin material or forces exerted on the exterior of the petal assembly 104 by the vaginal walls of the patient or by the user. Where metal materials are utilized, the petal assembly 104 can move between the expanded and the contracted configurations by flexing of the metal materials or by hinge mechanisms.

As noted above, the dilator 106 may be formed from plastic, metal or other materials. In the illustrated embodiment, the dilator is formed from a clear plastic resin material. The dilator 106 may have a generally cylindrical or conical configuration and is dimensioned to be received within the hollow interior of the petal assembly 104 at the proximal end 112 thereof. That is, the outside diameter of the dilator 106 (at least the proximal end thereof) is slightly smaller than the inside diameter of the petal assembly 104 at the proximal end 112. For example, the outside diameter of the dilator 106 at its proximal end thereof may be between about 1.5 and 2 inches.

The illustrated dilator 106 has a thumb grip 116 extending from the rear surface thereof. The thumb grip 116 can be gripped by the user to advance the dilator 106 into petal assembly 104 and to withdraw the dilator 106 from the petal assembly 104. In the illustrated embodiment, the dilator 106 includes a rib (not shown) extending from the bottom of the dilator 106. This rib and/or the bottom of thump grip 116 runs in a longitudinal dilator track 118 formed in an outer surface of the handle 102 so as to guide the longitudinal movement of the dilator 106. The thumb grip 116 may be ergonomically shaped and textured so as to facilitate operation by a physician or other user. In the case of a conical dilator 106 can be inserted, distal end first, into the petal assembly 104 to facilitate introduction of the petal assembly 104 into the introitus. The dilator can then be flipped and reinserted into the petal assembly 104 proximal (fat) end first to expand the petal assembly 104 to the extent desired. In the case of a cylindrical dilator 106, the dilator 106 would be advanced into the petal assembly 104 only after the petal assembly 104 is positioned within the introitus. In such cases, the petal assembly 104 may be bullet-shaped to better resist petal separation during introduction. In this regard, a cylindrical dilator 106 may facilitate better visualization as it provides a wide aperture across its entire length. The dilator 106 may be advanced linearly (and may thereafter maintain its position by friction or a ratchet mechanism) or may be threaded so as to advance into the petal assembly 104 via a rotary, screw-like motion.

The illustrated speculum 100 also includes a latex sleeve 120 to protect against penetration of the vaginal walls between the petals and potential pinching. As can be seen in FIG. 1B, the petals 107 are separated from one another by spaces in the expanded configuration. As the petals 107 collapse to the contracted configuration, the edges of the petals come together creating a risk that of tissue of a patient will be captured therebetween and pinched. This risk can be reduced by use of the optional latex sleeve 120. The latex sleeve 120 can be placed over the petal assembly 104 at one end thereof and unrolled like a condom to extend around substantially the entire external surface of the petal assembly 104. In this manner, the latex sleeve 120 guards against collapsing of the patient's uterine wall tissue into the spaces between the petals 107.

The handle 102 of the illustrated embodiment has a generally cylindrical configuration. If desired, the exterior surface of the handle 102 may be formed for improved ergonomics. The illustrated handle 102 has a hollow interior cylinder receptacle 122 dimensioned to receive a light source. The light source can be activated by the user to transmit light through the handle 102 and through the petal assembly 104 so as to illuminate a procedure site such as the patient's uterine walls and/or cervix. In the illustrated embodiment a light pipe 124 is formed in a portion of the petal assembly 104 to guide light to and concrete light on the procedure site. Conventional vaginal specula typically require an expensive custom light source. Though such light sources can be provided in connection with illustrated speculum 100, the illustrated speculum 100 can also be designed to receive an inexpensive pen light within the cylinder receptacle 122. The cylinder receptacle 122 may be formed so that the pen light is turned on, e.g., by depressing a button on the pen light, when the pen light is inserted into the cylinder receptacle 122. Alternatively, the pen light may have an on/off button exposed at a rear end thereof that can be accessed by the user after the pen light is inserted into cylinder receptacle 122.

Figure 2B:
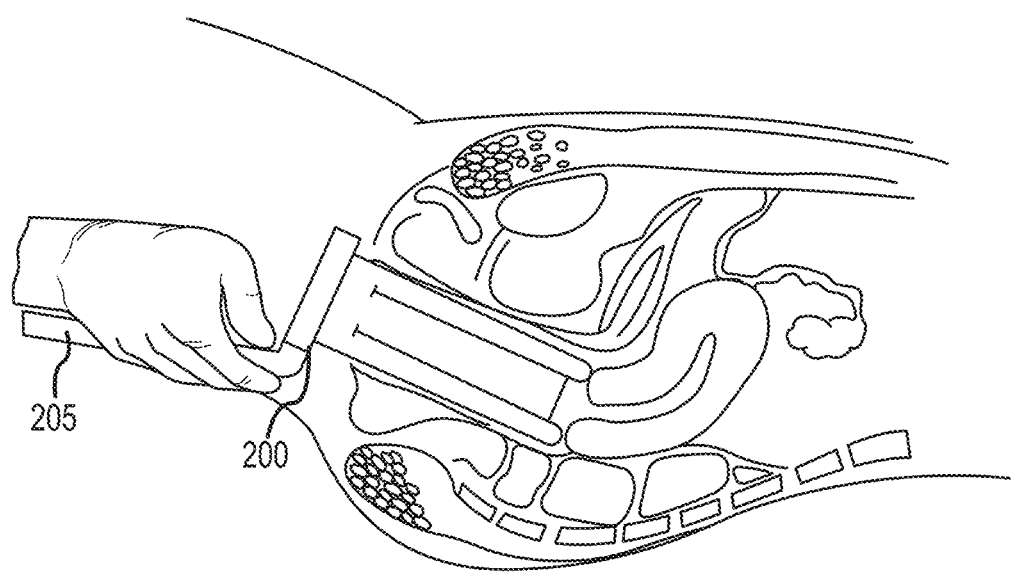

FIGS. 2A and 2B illustrate a speculum 200, generally similar in construction to the speculum 100 of FIGS. 1A and 1B but with a slightly different configuration, for use on a patient. Specifically, in use, the speculum 200 can be introduced into the introitus of the patient in a contracted configuration as shown in FIG. 2A. As shown, the speculum 200 is advanced into the patient until the distal end of the speculum 200 is adjacent to the patient's cervix 201. It will be appreciated that the speculum 200 is dimensioned appropriately in this regard. For example, the petal assembly 203 may have a length of about 6.5 inches and the handle 205 may have a length of about 3.5 inches for an overall speculum length of about 10 inches. Such dimensions are believed to accommodate a substantial range of physiological variability among patients. Once the speculum 200 has been inserted to the full extent desired, the physician or other user can advance the dilator 207 into the proximal end of the petal assembly 203 so that the petals of the petal assembly are radially separated.

It will be appreciated, that, in the case of a four petal assembly as described in connection with FIGS. 1A and 1B, two of the petals may separate along a front to back axis with respect to the patient and two of the petals may separate along a side to side axis with respect to the patient. This creates an unobstructed view. The petals may be formed to separate along other axes if desired. The user can then insert or otherwise activate a light source at the speculum handle 205 to illuminate the uterine walls and cervix of the patient. The physician or other user can then visually inspect the uterine walls and cervix of the patient by looking through the hollow interior of the dilator 207 and petal assembly 203 to obtain a clear view of the procedure site. When the inspection or any other desired procedure (e.g., obtaining an analysis sample by introducing an instrument through the hollow interior of the speculum) is complete, the dilator 207 is withdrawn from the petal assembly 203 allowing the petal assembly 203 to collapse to the contracted configuration. The speculum 200 can then be withdrawn from the patient's introitus and disposed of and or sterilized as appropriate.

FIGS. 3A-3G illustrates a speculum 300 constructed in accordance with alternative embodiment of the present invention. The speculum 300 generally includes a petal assembly 302 a handle 304 including a receptacle 306 for holding a light source 308 and a ratchet assembly 310 for use in expanding the petal assembly 302. The ratchet assembly 310 is operated using a thumb lever 312.

Figure 3A:
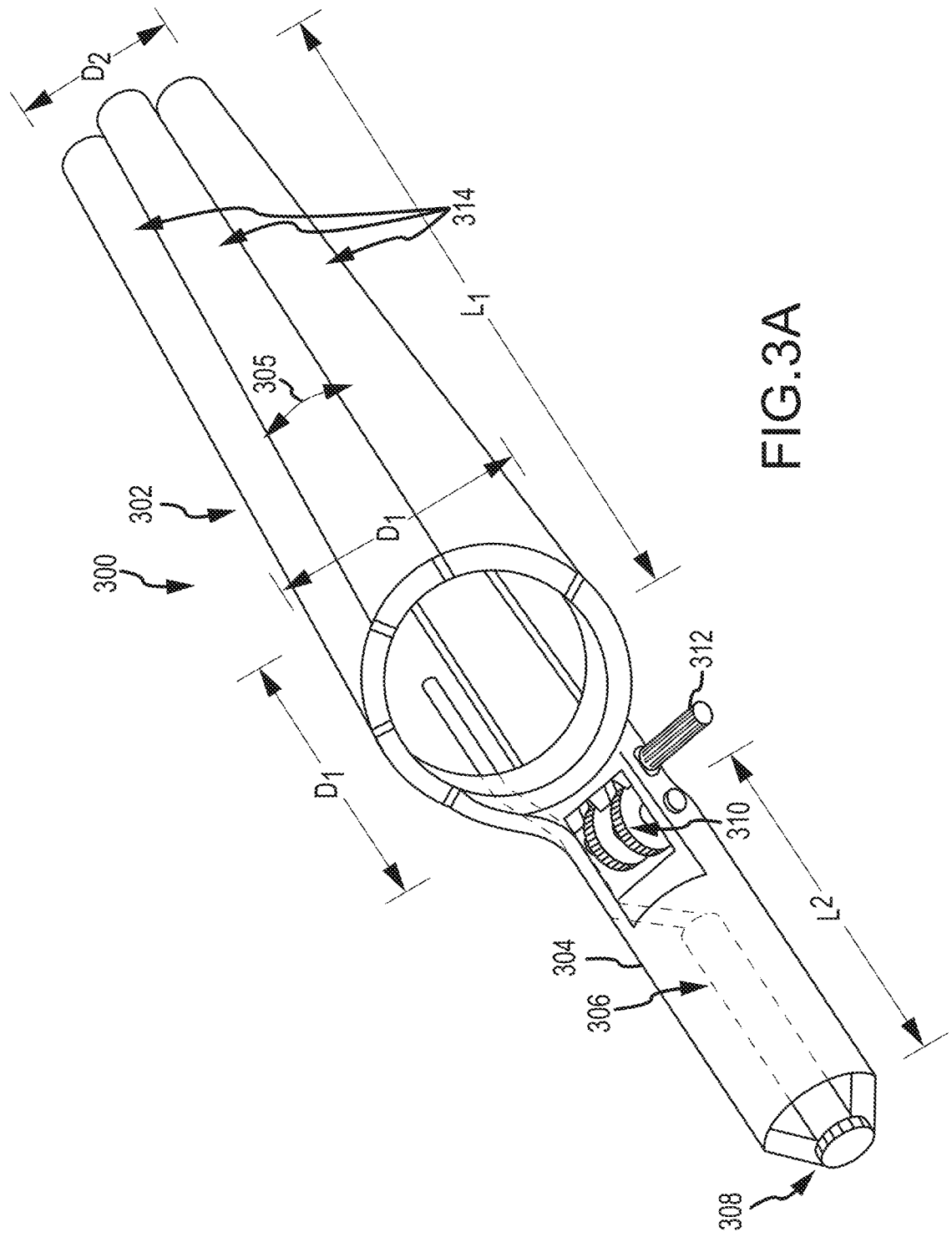
FIGS. 3A and 3B are perspective views of a vaginal speculum, in accordance with an alternate embodiment of the present invention, in expanded and contracted configurations, respectively.
Figure 3B:
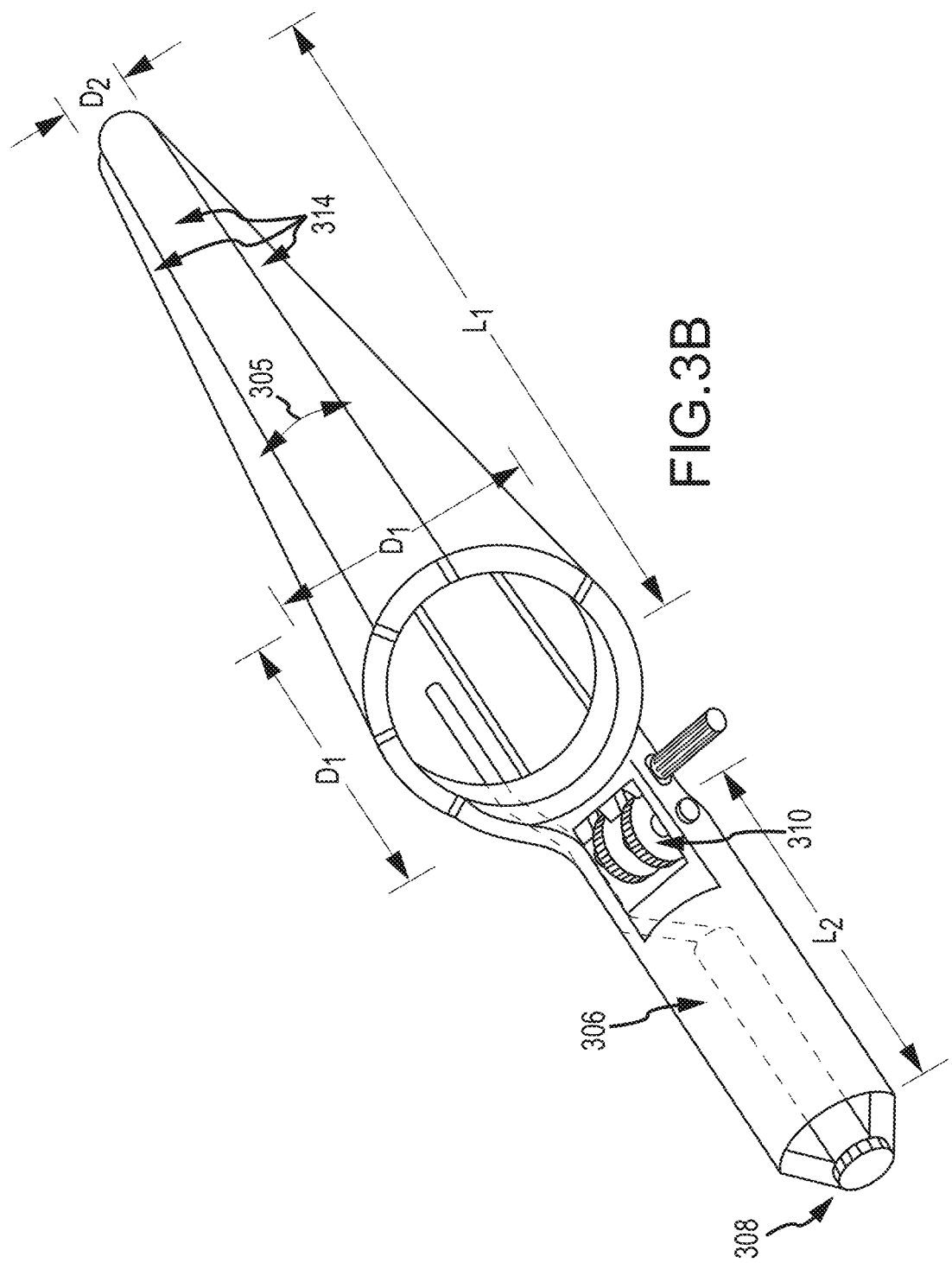
Figure 3C:
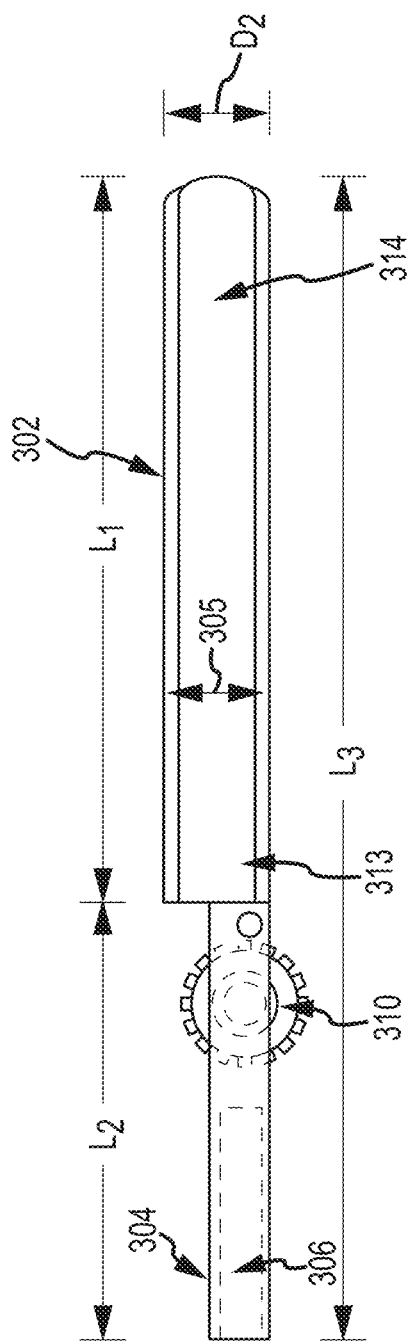
FIG. 3C is a side view of the speculum of FIGS. 3A-3B in the contracted configuration.
Figure 3D:
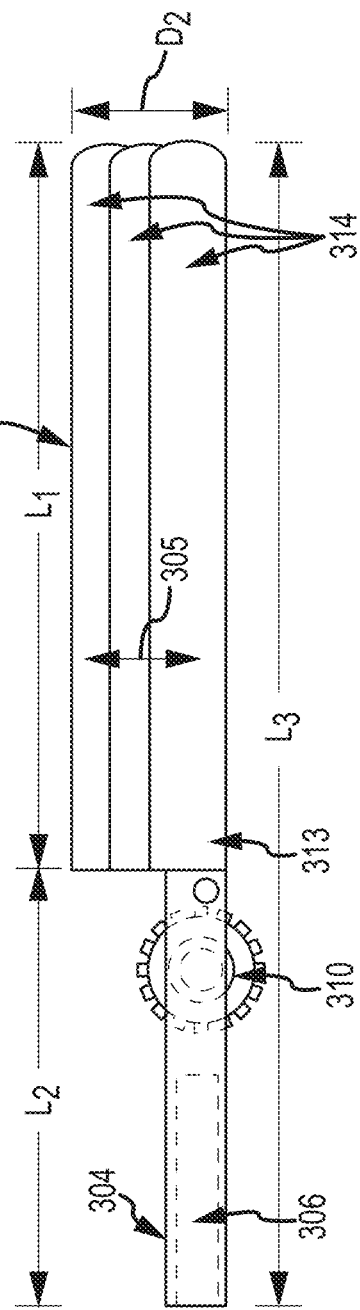
FIG. 3D is a side view of the speculum of FIG. 3A in the expanded configuration.
Figure 3E:
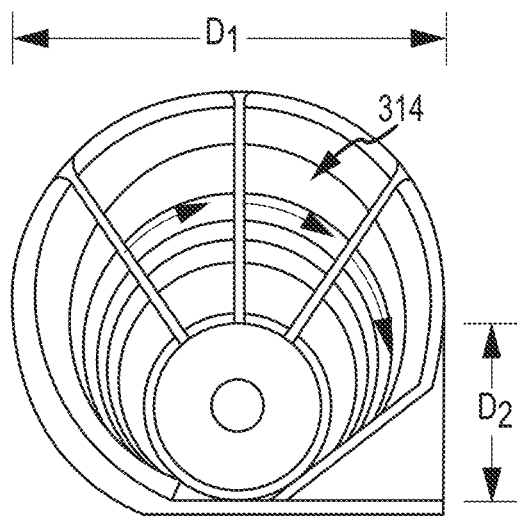
FIG. 3E is a end view of the dilation assembly of the speculum of FIGS. 3A-3B.

The speculum 300 of FIGS. 3A-3E shares many characteristics with the speculum of FIGS. 1A and 1B. For example, the speculum 300 is used by inserting the petal assembly 302 into the patient's introitus with the speculum 300 in a contracted configuration (as shown in FIGS. 3B and 3C). The speculum 300 is then expanded to the dilated configuration (as shown in FIGS. 3A and 3D). The light source 308 can then be activated to illuminate patient's vaginal walls and cervix which can be inspected visually by looking through the hollow petal assembly 302. Moreover, like the embodiment of FIGS. 1A and 1B, the speculum 300 expands radially with respect to multiple axes for improved viewing without interference due to collapsing vaginal walls.

However, the speculum 300 has some differences in relation to the embodiment of FIGS. 1A and 1B. In particular, whereas the petals in FIGS. 1A and 1B are separated by spaces at least in the expanded configuration, the petals 314 of the speculum 300 overlap as can best be seen in FIGS. 3E and 3G. When the petal assembly 302 is expanded or contracted, the petals slide circumferentially over one another (as generally indicated by arrows 305) in manner analogous to a collapsible colander. Accordingly, there are no spaces between the petals in either the expanded contracted configuration. This may further protect against collapsing of the vaginal walls and potential pinching.

Figure 3G:
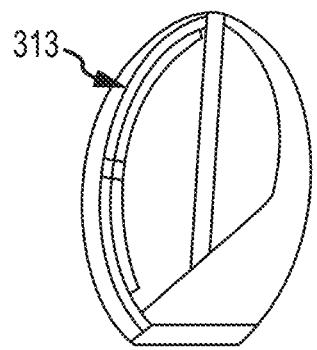
FIG. 3G is a expanded view of the linkage for interconnecting the worm gear racket assembly to the dilation assembly of the speculum of FIGS. 3A and 3B.
Figure 3F:
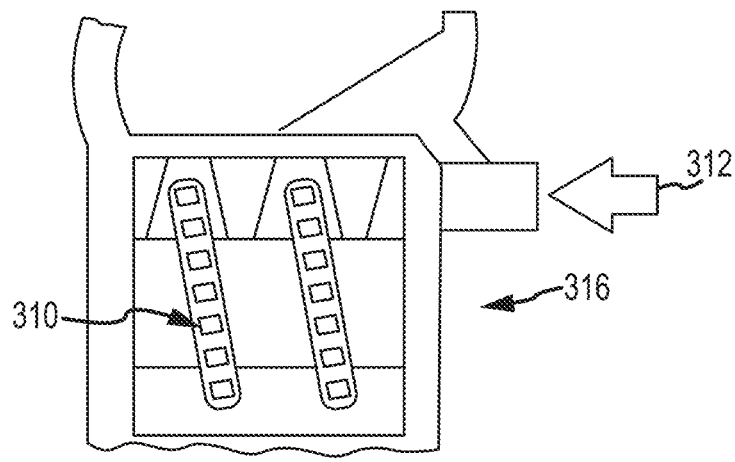
FIG. 3F is a expanded view of the worm gear ratchet mechanism of the speculum of FIGS. 3A and 3B.
Figure 4A:
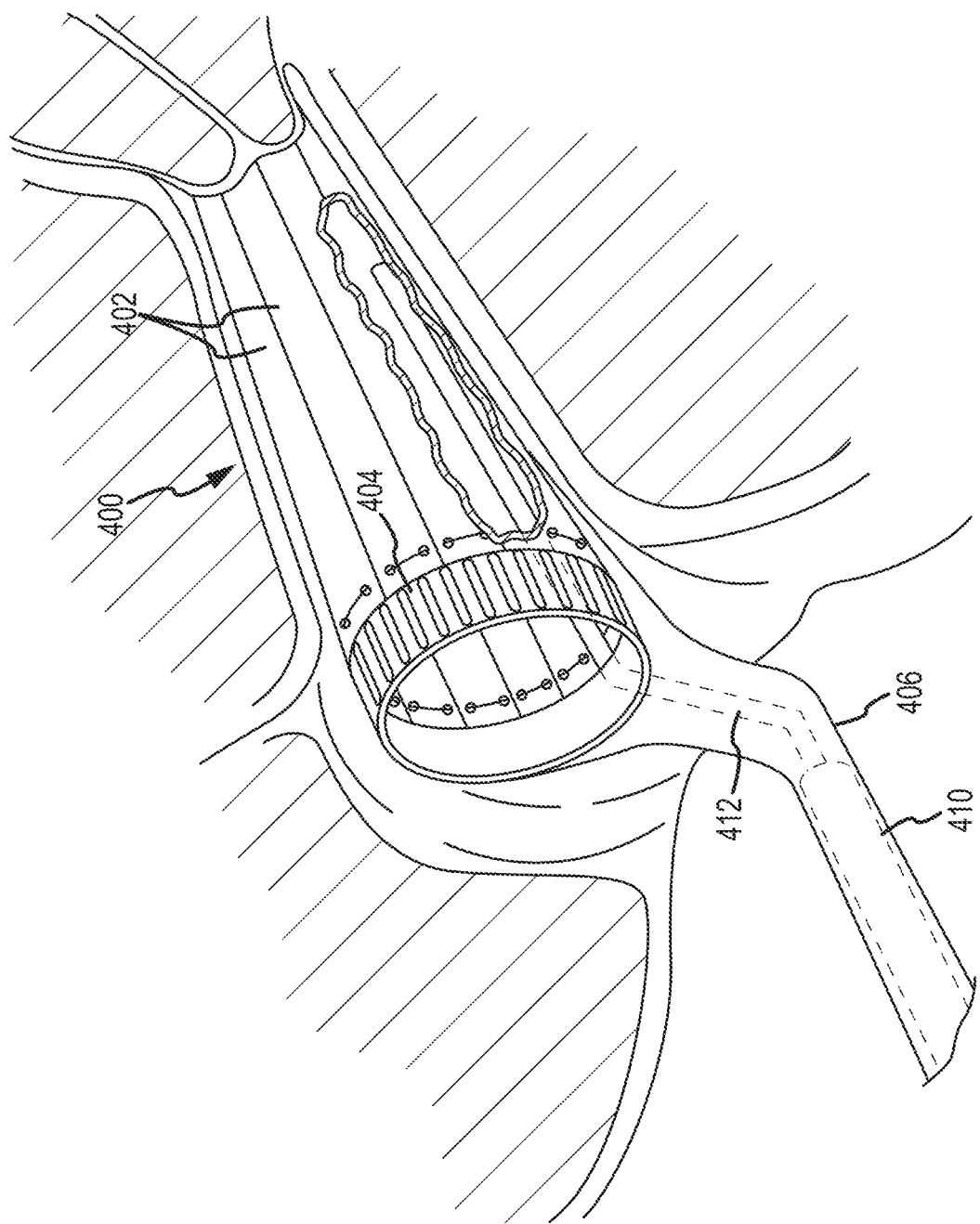
FIG. 4A shows a speculum, in accordance with a still further embodiment of the present invention, positioned for inspection of a patient's cervix.
Figure 4B:
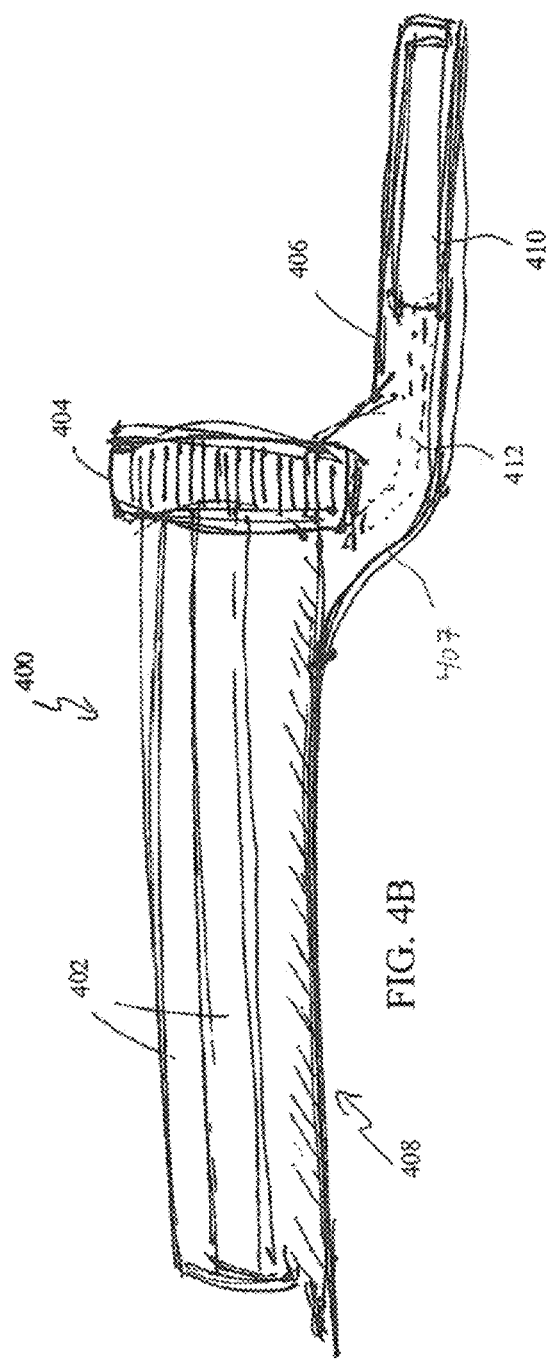
FIGS. 4B-4C are side views showing the speculum of FIG. 4A in the open and closed configurations respectively.
Figure 4C:
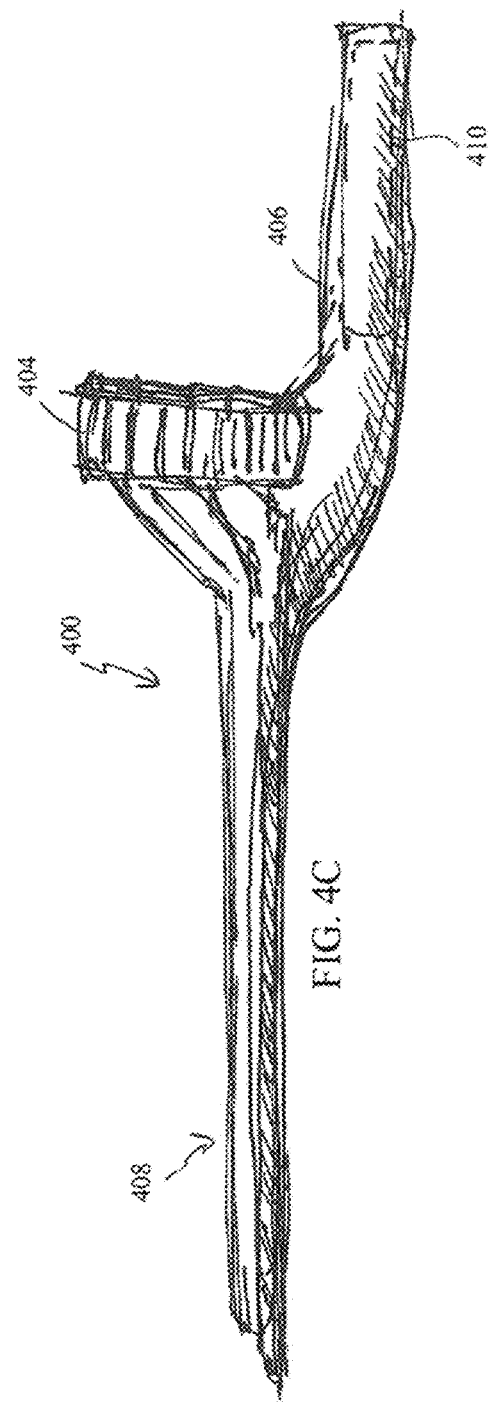

Another difference between the illustrated speculum 300 and that of FIGS. 1A and 1B is the mechanism for actuating expansion of the petal assembly 302. Specifically, the petal assembly 302 is expanded by operation of the thumb lever 312. The thumb lever 312 interfaces with a worm gear ratchet as shown in FIG. 3F such that depressing the thumb lever closes the speculum 300 to the contracted configuration and pulling outwardly on the thumb lever 312 causes the speculum 300 to be expanded to the dilated configuration. The thumb lever 312 causes the worm gear of ratchet assembly 316 to rotate. The worm gear ratchet assembly 316 is then connected to the proximal ends 313 of the petals 314 by appropriate linkage (as shown in FIGS. 3F and 3G) to expand and contract the petal assembly 302 as desired.

The illustrated speculum 300 is dimensioned to accommodate a range of patients including larger patients. For example, the diameter $D_1$, of the proximal end of the petal assembly 302 may be about 1.5 inches. The diameter, $D_2$, of the distal end of the petal assembly may be about 1.4 inches in the expanded configuration and about 0.7 inches in the contracted configuration. The petal assembly 302 has a length, $L_1$, of about 6.5 inches and the handle 304 has a length, $L_2$, of about 3.5 inches for an overall length, $L_3$, of about 10 inches for the speculum 300.

FIGS. 4A-4E illustrate a still further embodiment of a speculum 400 in accordance with the present invention. The speculum 400 includes a number of overlapping speculum petals 402 generally similar to the petals in the embodiment of the FIGS. 3A-3G. In this case, however, the petals are expanded and contracted directly by rotating retention ring 404 rather than using a ratchet assembly as described in connection with the embodiment of FIGS. 3A-3G. In addition, the handle 406 is offset vertically, by offset structure 407, from the expansion assembly 408 which may facilitate visual inspection through the expansion assembly 408. The handle 406 further includes a receptacle 410 for receiving a light source and a light pipe 412 for directing light from the source to the patient's cervix.

FIGS. 5A-5F illustrate a speculum 500 in accordance with a still further embodiment of the present invention. The speculum 500 is similar to the speculum 100 of FIGS. 1A-1B, with some additional features shown and minor differences in configuration. The speculum 500 generally includes: a generally conical petal assembly 502 including a number of petals 504; a generally cylindrical dilator 506 for expanding the petal assembly 502 and allowing it to contract; and a handle 508 including a receptacle 510 for receiving a light source 512. As discussed above, the speculum can be formed, for example, from clear plastic or metal as desired.

The illustrated petals 504 are formed in an overlapping, collapsible configuration. That is, adjacent petals 504 extend circumferentially over one another, and slide over one another as the petal assembly 502 is expanded and contracted. In this manner, gaps between the petals 504 are avoided, even in the expanded configuration, thus reducing the likelihood that tissue of the patient will be pinched due to operation of the speculum 500.

The speculum 500 further includes a ratchet mechanism 514 for advancing and withdrawing the dilator 506 into and out of the petal assembly 502. The ratchet mechanism 514 includes a ratcheted handle surface 516 that interfaces with a bottom of a thumb lever 518. The thumb lever 518 includes an advance surface 520 and a release surface 522. The physician or other user can press on the advance surface 520, as generally indicated by arrow 524, to move the thumb lever 518 forward. The thumb lever 518 presses against the dilator 506 so that it also moves forward thus expanding the petal assembly 502. The ratchet mechanism 514 is then effective to hold the speculum in the expanded configuration.

To release the ratchet mechanism 514 so that the dilator 506 can be withdrawn from the petal assembly 502 to close the petals 504, the user can press on the release surface 522 as generally indicated by arrow 526. This causes the rear edge of the thumb lever 578 to lift and disengages the ratchet mechanism 514. The user can then slide the thumb lever 518 rearwardly to withdraw the dilator 506 from the petal assembly 502.

As noted above, the handle 508 includes a receptacle 510 for receiving a light source 512. Although any appropriate light source can be used, the illustrated receptacle 510 can receive a low-cost pen light type of light source 512, thereby reducing costs and inconvenience in relation to some conventional systems. The light source 512 may have an on/off button at its rear end that can be easily accessed by the user during a procedure. Light from the light source is guided through the handle 508, and directed through the petal assembly 502 to the procedure site by a plastic light pipe 528. Optionally, a brightly colored tag 530 or strap may be attached to the light source 512 to assist in locating the light source and to remind the user not to accidentally dispose of the light source 512 when the speculum 500 is discarded after a single use.

The petals 504 of the illustrated speculum 500 overlap, as indicated by arrow 532, so that there are substantially no spaces between the petals 504 in the dilated configuration. In this regard, the petals 504 may move linearly (or arcuately with substantially no circumferential component) in a radial direction when expanding while maintaining their overlapped, stacked relationship at their proximal ends like flower petals, or the petals 504 may slide circumferentially over one another while expanding like an expandable colander.

Figure 5C:
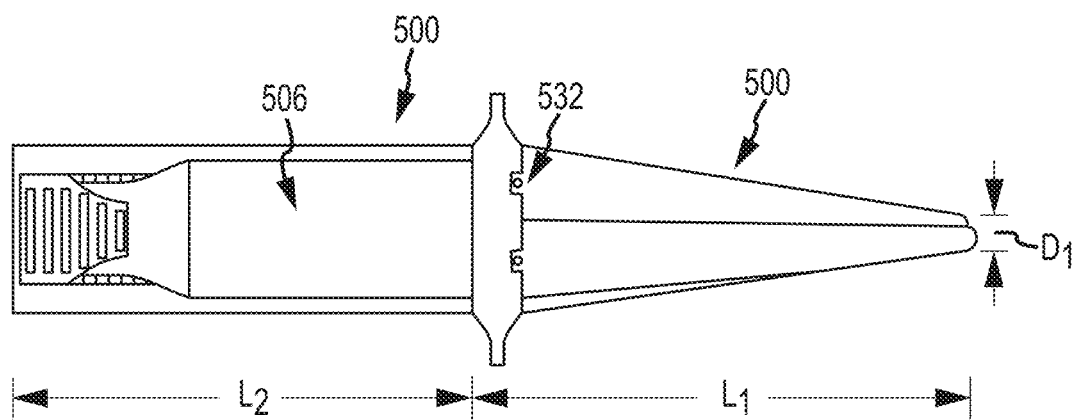
FIGS. 5C-5D, are top views of the speculum of FIGS. 5A-5B in the closed and open configurations, respectively.
Figure 5D:
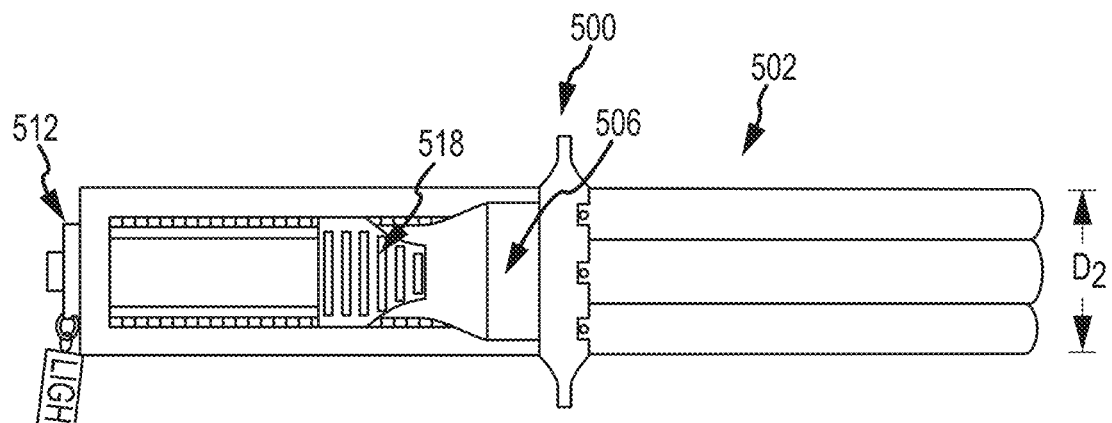
Figure 5E:
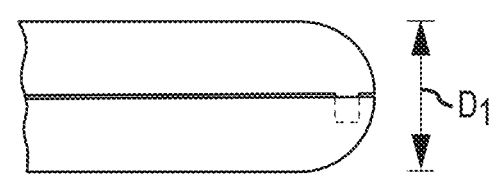
Figure 5F:
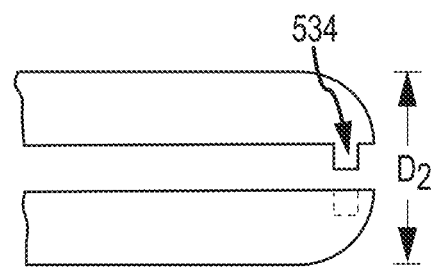

The speculum 500 is preferably dimensioned to accommodate a range of patients. For example, the petal assembly 502 may have a length $L_1$, of about 3.5 inches and the handle 508 may have a length, $L_2$, of about 3.5 inches for an overall speculum length of 7 inches. In the contracted configuration, the distal end of the petal assembly 502 has a diameter, $D_1$, of about 1.5 inches. The distal end of the petal assembly 502 preferably has a bullet-shaped configuration, as can be seen in FIG. 5E, that helps maintain the petal assembly 502 in the contracted configuration as the petal assembly 502 is introduced into the introitus. Optionally, one or more pegs 534 and mating receptacles may be provided at the distal end of the petal assembly 502 to further assist in maintaining the contracted configuration.

In the various embodiments disclosed above, the handles generally extend rearwardly in alignment with or at an acute angle to the longitudinal axis of the petal assembly in each case.

Another embodiment of a speculum 600 in accordance with the present invention is shown in FIGS. 6A-9B. The speculum 600 generally includes a speculum body 602 and a dilator 604. The speculum body 602, in turn, includes a petal assembly 606 and a handle 608.

Figure 6A:
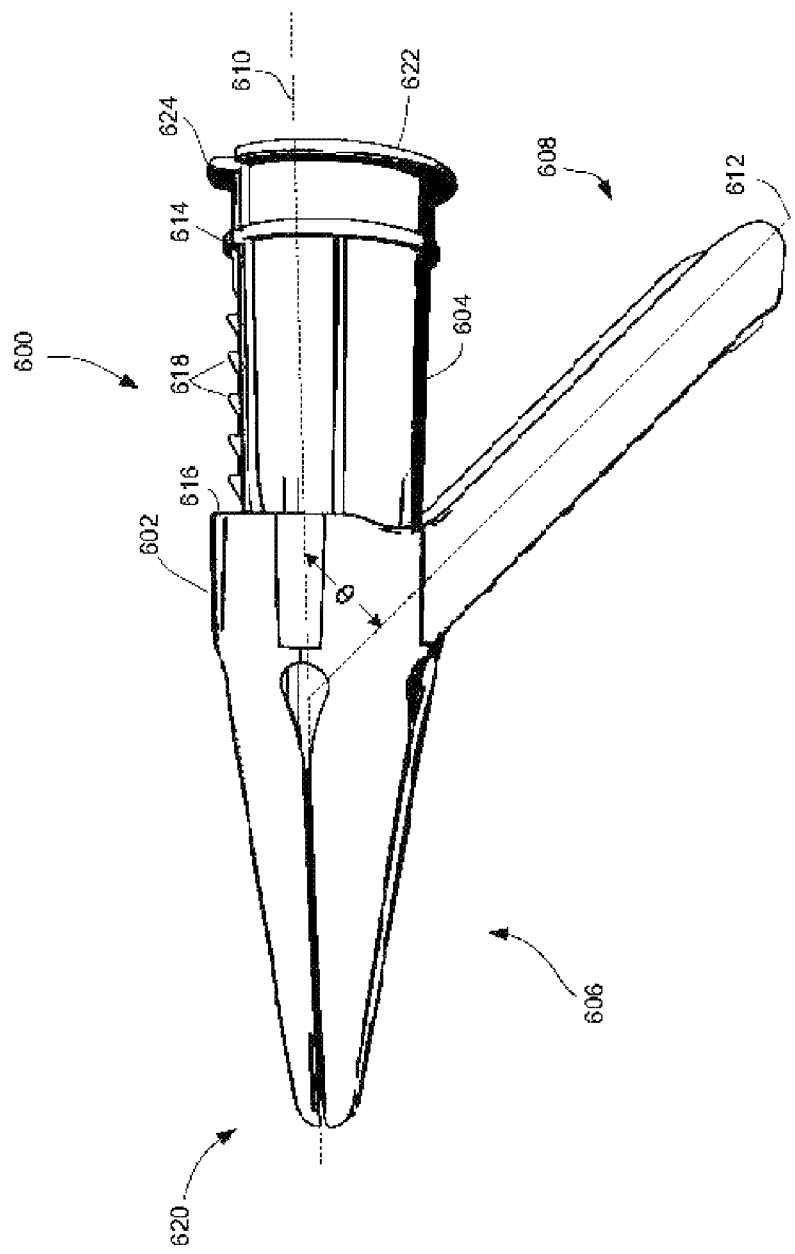
FIG. 6A is a side view of a speculum constructed in accordance with the present invention in a contracted configuration.
Figure 6B:
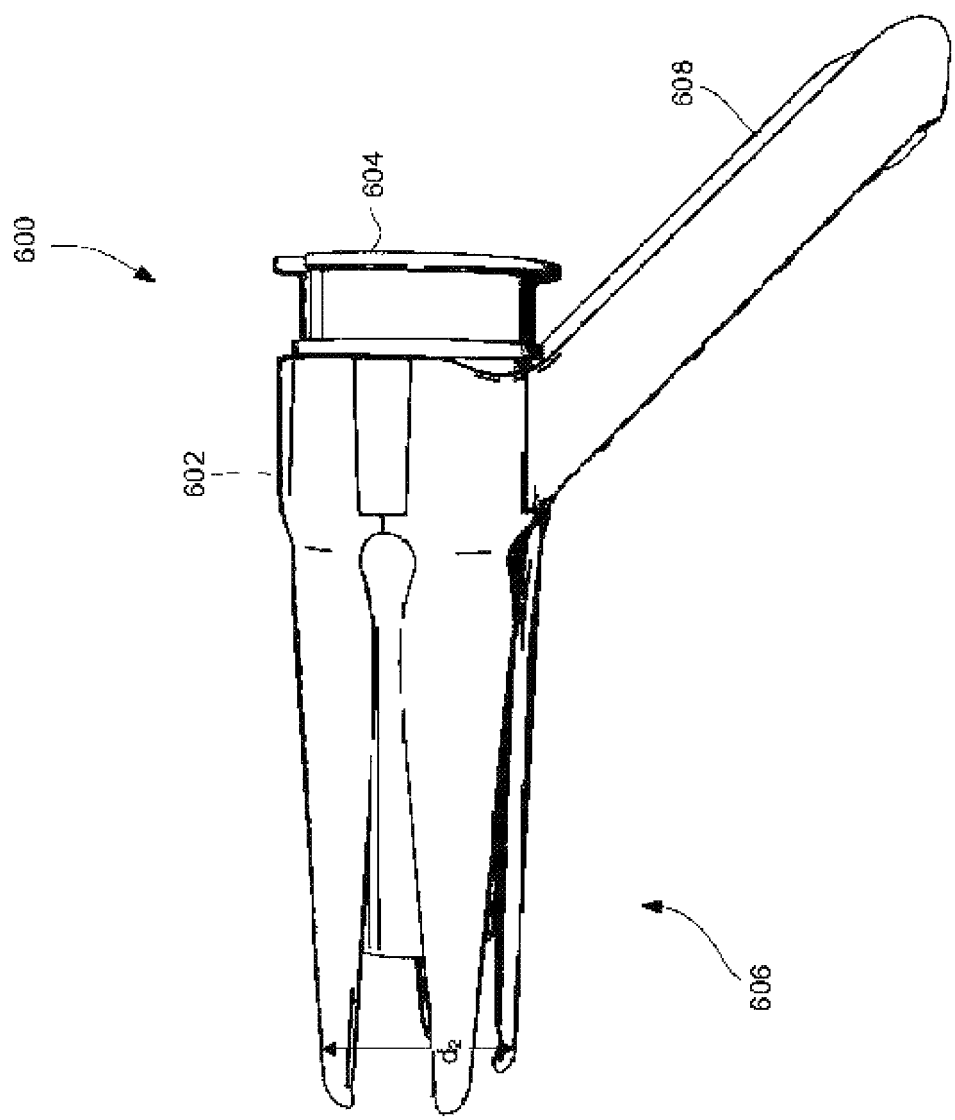
FIG. 6B is a side view of the speculum of FIG. 6A in a dilated configuration.

FIG. 6A shows the speculum 600 in a retracted configuration and FIG. 6B shows the speculum 600 in a dilated configuration. The speculum 600 is moved between the retracted and dilated configurations by advancing or withdrawing the dilator 604 relative to the speculum body 602 along the longitudinal axis 610 of the speculum 600. In the fully inserted position of the dilator 604, corresponding to the fully dilated configuration of the speculum 600, the collar 614 of dilator 604 buts against the rear surface 616 of the speculum body 602. The dilator 604 also includes ratchet teeth 618 that allow the dilator 604 to be positioned in various intermediate positions between the fully inserted and fully retracted positions. Such intermediate positions may be preferred depending, among other things, on the anatomy of the patient and the procedure being performed.

In operation, a user, who may be a physician, physician's assistant, clinic staff member or other person, can insert a light source 607 (FIG. 9B) into the handle 608, as will be described in more detail below, and turned the light source on. A sheath formed from latex or other suitable material may be applied around the forward end of the speculum 600, if desired, and a lubricant may be applied to the sheath or forward end. The user can then grip the speculum 600 using the handle 608 and advance the forward end 620 of the speculum 620 into the patient and advance the speculum 600 until the speculum 600 meets resistance. At that point, the user may press against the rear flange 622 of the dilator 604, for example, using the thumb of the same hand that grips the handle 608 or the user's other hand, and advances the dilator 604 in relation to the speculum body 602 to the desired position. Various procedures can then be performed as will be discussed in more detail below. At the conclusion of the procedure or procedures, the user can depress the ratchet release lever 624, for example, using the thumb of the same hand that grips the handle 608 or the user's other hand, allowing the dilator 604 to be withdrawn from the speculum body 602 to reach the fully retracted configuration. The speculum 600 can then be readily withdrawn from the patient.

The handle 608 of the illustrated speculum 600 is angled in relation to the petal assembly 606. More specifically, the handle 608 is oriented such that an angle, θ, that is less than 90°, is defined between the longitudinal axis 612 of the handle 608 in relation to the longitudinal axis 610 of the speculum 600 and petal assembly 606. Conventional specula have handles that are oriented perpendicular to the longitudinal axis of the speculum. This is customary and works well when the patient is reclined on an appropriate examination table. However, in many cases, including clinics in geographies where medical resources may be more limited, such an examination table may not be available. Moreover, the illustrated angled configuration facilitates convenient access to the dilator 604. At the same time, the angled configuration positions the user's hand on the handle 608 outside of a line of viewing and access to the patient generally corresponding to the longitudinal axis 610. It is noted that some of these considerations can alternatively be addressed by providing a handle that is generally aligned with the longitudinal axis of the speculum but is offset from the longitudinal axis of the speculum by depending structure extending between the handle and the speculum body as generally shown above.

In the illustrated embodiment, the angle, θ, is less than 75°. More preferably, the angle is between about 30°-75°. Most preferably, the angle is between about 40°-60°. In the illustrated embodiment, the angle is about 50°.

Figure 7A:
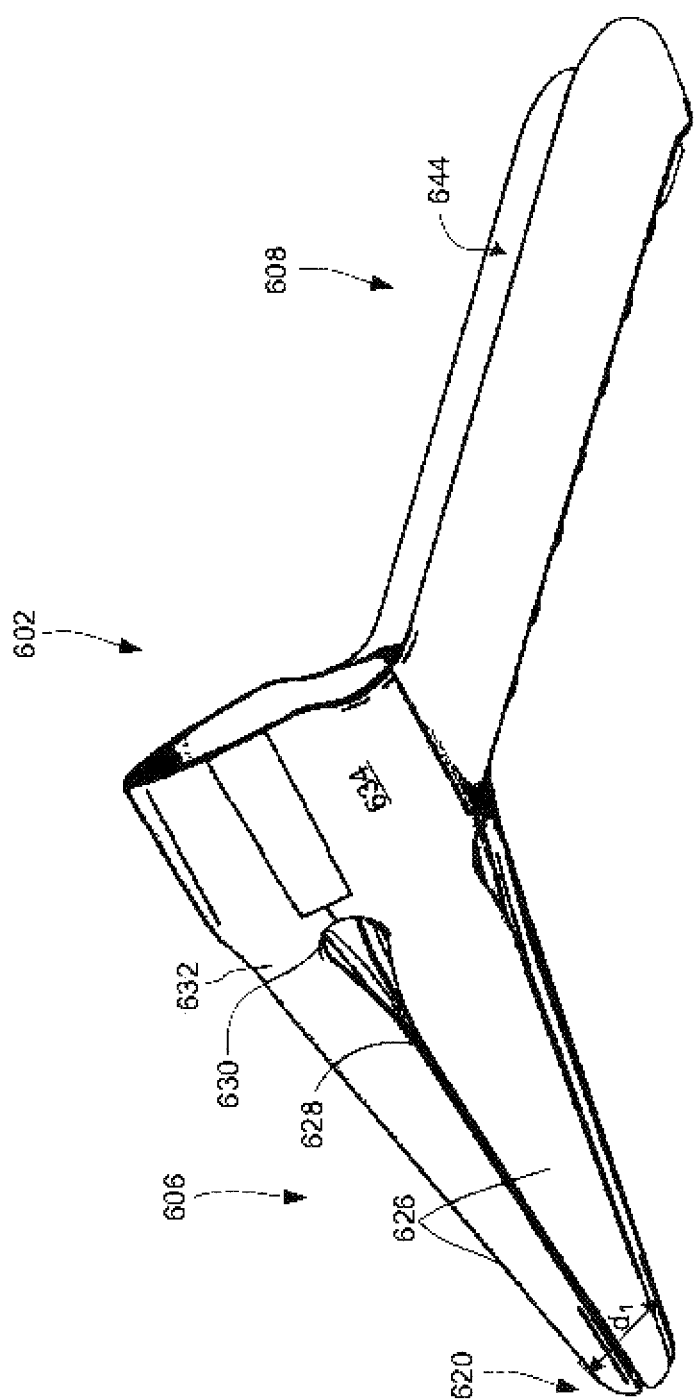
FIG. 7A is a perspective view of a speculum body of the speculum of FIG. 6A.
Figure 7B:
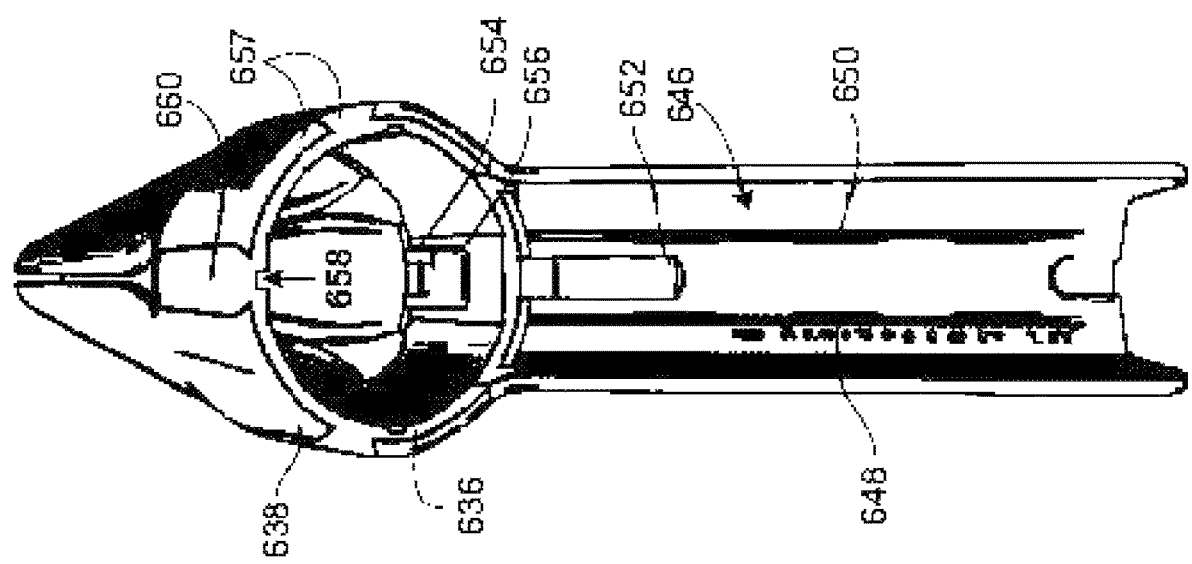
FIG. 7B is a rear perspective view of the speculum of FIG. 6A.
Figure 7C:
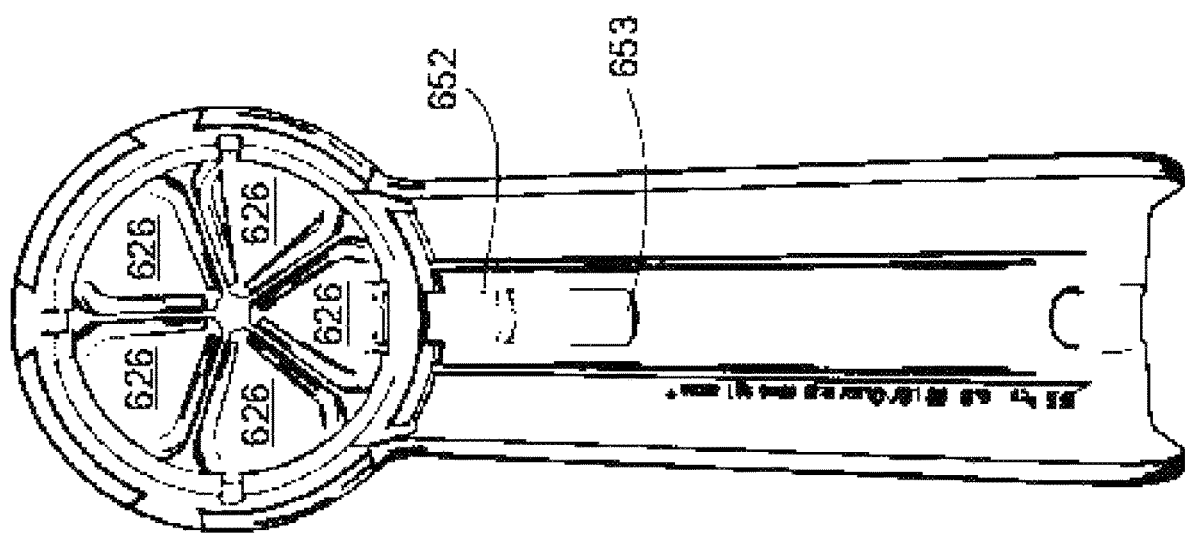
FIG. 7C is a rear view of the speculum of FIG. 6A.
Figure 7D:
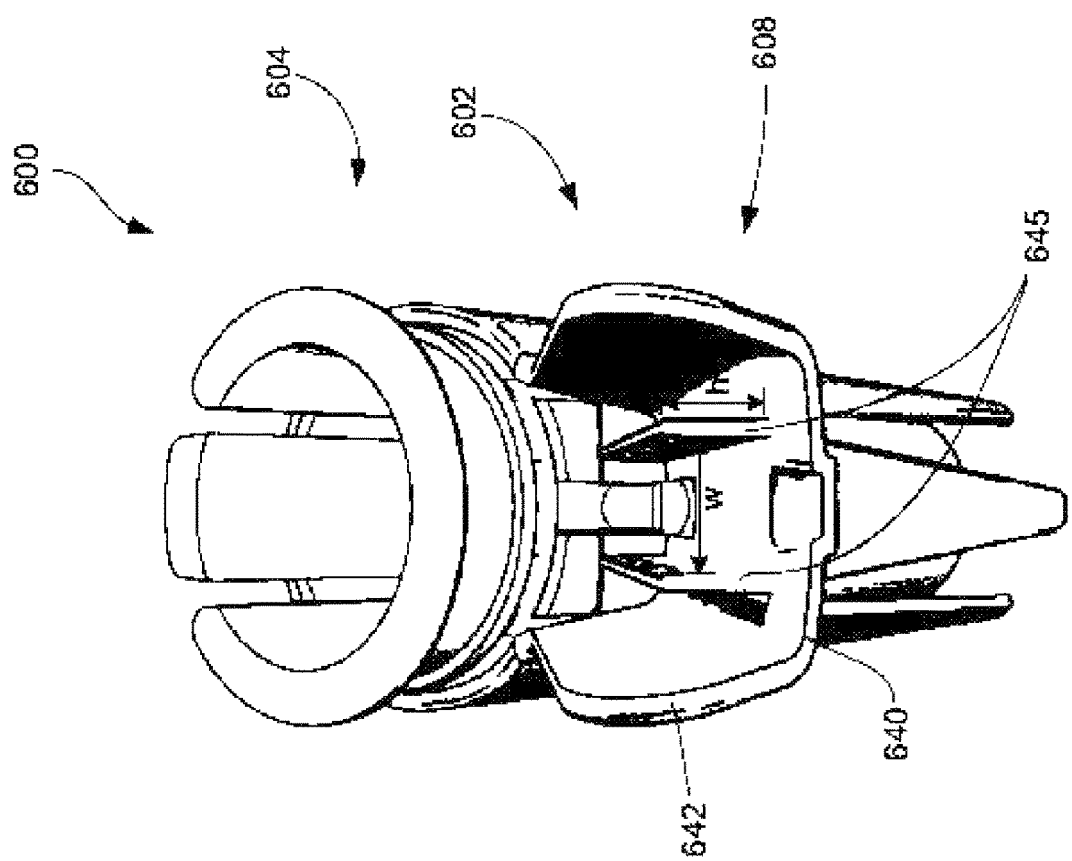
FIG. 7D is a perspective view of the speculum of FIG. 6A.
Figure 7F:
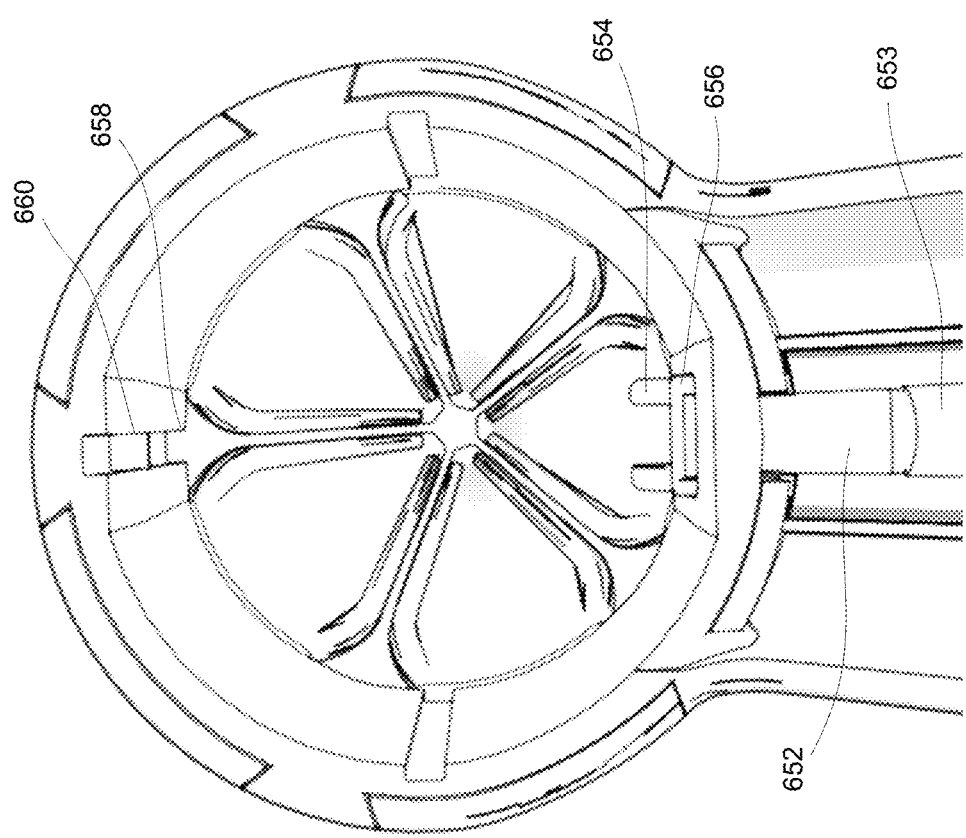
FIG. 7F is an enlarged perspective view of a portion of the speculum of FIG. 6A.

FIG. 7A-7E show various views of the speculum body 602. More specifically, FIGS. 7A-7C show the speculum body 602 alone in order to better illustrate certain features whereas FIG. 7D shows the full speculum 600 including the speculum body 602 and the dilator 604. FIG. 7E shows an expanded view of certain portions of the speculum body 602. As shown, the speculum body 602 includes the petal assembly 606 and the handle 608. The petal assembly 606 includes a number of petals 626. The number of petals 626 may vary, but the assembly 606 will generally include at least three petals 626 so as to allow for dilation relative to more than one axis for improved treatment site visualization and access. The assembly 606 may have many petals with the upper limit being determined by practical considerations such as ensuring that each petal 626 is sufficiently strong or stiff so as not to collapse under pressure from the vaginal walls. This will depend on a number of factors including materials, any stiffening structure formed in the petals 626, and the amount of support provided by the dilator 604 when inserted into the assembly 606. In the illustrated embodiment, five petals 626 are provided in the petal assembly 606.

At the forward end 620 of the assembly 606, each of the petals 626 is rounded and turned inwardly toward a centerline (generally corresponding to the axis 610 of FIGS. 6A-6B) so as to define a blunt nose shape to the forward end 620 for improved penetration and patient comfort. The petals 626 are separated by slots 628. The slots 628 are shaped such that the edges of adjacent petals 626 are substantially abutting when the petal assembly 606 is in the fully retracted position. In this manner, the risk of pinching during insertion and withdrawal is reduced. The edges of the petals 626 may also be slightly rounded or otherwise shaped so as to reduce pinching during transition from the dilated configuration to the retracted configuration of the assembly 606. In addition, as shown, the base 630 of each of the slots 628 may be rounded so as to eliminate stress points and potential cracking of the speculum body structure.

As noted above, the petals 626 are turned inwardly at the front end 620 to define a blunt nose shape. Specifically, the petals 626 may turn inwardly over the last 0.25 inches adjacent the tips of the petals 626. At the start of this turn, the front end may have a diameter $d_1$ (FIG. 7A), of no more than about 0.75 inches, for example, about 0.5 inches, in the contracted configuration, and a diameter, $d_2$ (FIG. 6B), of at least 1.5 inches, for example, about 1.75 inches, in the dilated configuration.

In addition, the length of the handle 608 may be between about 3-6 inches, for example, between 4-5 inches. In the illustrated embodiment, the handle is about 4.25 inches. At least the external surface of the handle base 640 may include ribs or other contouring for improved gripping and ergonomics. The overall length of the petal assembly 606 may be between about 4-7 inches, for example, between about 5-6 inches. The illustrated assembly is about 5.5 inches long. The individual blades 626 may be between about 4-5 inches, for example, about 4.5 inches. The illustrated blades have a maximum width of about 0.8-0.9 inches. The thickness of the plastic forming the speculum 600 may be about 0.06-0.15 inches with the thickness varying, e.g., to define flex points.

The overall length of the dilator 604 may be between about 4-7 inches, for example, between about 5-6 inches. The illustrated dilator is about 5.25 inches long. The length from the collar 614 to the front end of the dilator 604 may be between about 4-5 inches, for example, about 4.5 inches. The diameter of the dilator 604 is selected to extend within and expand the blade assembly 606. As noted above, the diameter of the dilator 604 may taper over at least a front section thereof. In the illustrated embodiment, the inside diameter of the dilator 604 at the back end may be about 1.5-1.6 inches and the inside diameter at the front end may be about 1.1-1.2 inches. While the noted dimensions are believed to be suitable to accommodate a large range of patients, the speculum 600 may be provided in other sizes, e.g., for young or small patients (or larger patients).

The petal assembly 606 is connected to the handle 608 via a reinforced central section 634. Hinge portions 632 may be defined where each of the petals 626 meets the central section 634. In the illustrated embodiment, the speculum body 602 is formed from molded plastic. The hinge portion 632 is provided at a narrowed area of each of the petals 626 corresponding to the widened base 630 of the slots 628. The thickness of the plastic may be slightly reduced at the hinge portion 632 to define a fabric hinge. The fabric hinge 632 thus defines the principal location of flexion associated with moving between the dilated and retracted configurations of the assembly 606. More specifically, when the dilator 604 is advanced forwardly so that the forward edge of the dilator 604 extends beyond the hinge portion 632 the dilator 604 begins to press outwardly against the inner surfaces of the petals 626 causing the petals 626 to flex outwardly at the hinge portion 632.

As best seen in FIG. 7D, the handle 608 has a generally U-shaped cross-section defined by a base 640 and sidewalls 642 with an open top 644. A light source receptacle 646 is provided in the interior area of the handle 608. The receptacle 646 is defined by receptacle walls 648 and 650. The walls 648 and 650 are generally parallel and are otherwise configured to receive a light source, such as a penlight, therebetween. In this regard, the walls define a receptacle that has a width, w, and a height, h, selected to securely receive a cylindrical penlight therein. The particular dimensions may be selected to accommodate the desired penlight. In this regard, penlights are typically generally cylindrical in shape and have a diameter selected to securely hold a AAA battery that is often used as a power source. As the AAA battery has a diameter of 0.41 inches, the penlight diameter is generally slightly larger. In the illustrated embodiment, the width, w, of the receptacle and the height, h, of the receptacle are each about 0.4-0.6 inches, for example, about 0.47 inches. The length of the receptacle is about 3-4 inches. The receptacle 646 thus accommodates a variety of penlights that are commercially available including penlights having a diameter of between about 0.45-0.6 inches and a length of between about 3-6 inches.

Each of the walls 648 and 650 further includes continuous or intermittent retaining members 645 for retaining the light source in the receptacle 646. The members 645 are disposed adjacent the upper ends of the walls 648 and 650 away from the base 640 of the handle 608, and extend slightly inwardly toward the center of the receptacle 646 and towards the opposing wall. The plastic walls 648 and 650 can flex sufficiently to allow the light source to be inserted into the receptacle 646 via the open top 644 of the handle 608 such that the light source snaps into place in the receptacle. Alternatively, the light source can be inserted into the receptacle 646 longitudinally by sliding the light source along the length of the receptacle 646.

The open top configuration of the handle 608 and receptacle 646 also allows access to on/off switches of light sources that are located on the rear end of the light source or on a side surface of the light source thus providing additional flexibility in selecting a light source, e.g., to reduce costs. A stop 652 at the forward end of the receptacle 646 defines the forwardmost position of the light source in the receptacle 646. In this manner, the sidewalls 648 and 650 together with the stop 652 ensure proper positioning of the light source so that the light source is aligned as desired with the light directing block 656 as will be described in more detail below. In this regard, the stop 652 extends upwardly from the base 640 of the handle 608 sufficiently to engage and stop the light source but without blocking light from the light source. The illustrated stop 652 has a generally semicircular cross-section and is received within a correspondingly shaped recess 653 formed in the base 640 of the handle 608.

The central section 634 connects the handle 608 to the petal assembly 626, serves as a mounting structure for various elements as will be described below, and receives the dilator 604. Accordingly, the central section 634 will bear substantial forces in operation and needs to be sufficiently strong and stiff. In this regard, the central section 634 may be formed from stronger materials, may be thicker, may be structurally reinforced, or otherwise provided with sufficient strength to perform the noted functions. In the illustrated embodiment, the central section 634 is formed from inner 636 and outer 638 members that collectively thicken and reinforce the central section 634 as well as simplifying manufacturing. The inner member 636 and outer member 638 include complementary tongue and groove connections 657 that allow for convenient sliding interconnection as well as proper alignment and orientation of the members 636 and 638. A groove 658 formed in the inner member 636 receives the ratcheting teeth 618 (FIG. 6A) of the dilator 604 and a recess 660 formed in the groove 658 allows each tooth 618 to register and lock into position. For example, the teeth 618 may be spaced so as to correspond to 0.125-0.25 inch measurements in dilation diameter of the petal assembly 606. The inner member 636 and outer member 638 also have slots formed therein for receiving the light directing block 656 including the dilator retaining guides 654 as will be described in more detail below.

FIG. 7E shows expanded perspective views of the light directing block 656 and the stop 652. Although these components are illustrated as separate pieces, the block 656 and stop 652 may be formed as a single integral unit or both the block 656 and stop 652 may be integrally formed (e.g., molded) as part of the speculum housing 602. In the illustrated implementation, the block 656 is provided as a separate molded plastic piece that is placed in position and fused or bonded to the base of the central portion 634 of the speculum housing 602. Similarly, the illustrated stop 652 is provided as a separate molded plastic piece that can be received in the channel 653 of the handle 608 and can then slide forward in the channel until it abuts the bottom of the block 656. The stop 652 can then be fused or bonded in the desired position.

The illustrated block 656 includes stop retaining guides 654. As will be understood from the description below, the guides 654 extend through a slot formed on the bottom surface of the dilator to guide the sliding motion of the dilator 604 through the petal assembly 606. In addition, the front surfaces of the guides 654 abut against the rear surface of the slot formed in the dilator 604 to define the forward-most position of the dilator 604 with respect to the petal assembly 606. The forward surface of the guides 654 also abut against the forwardmost end of the slot formed in the dilator 604 to define the fully retracted position of the dilator 604 with respect to the petal assembly 606 and to prevent inadvertent separation of the dilator 604 from the speculum body 602.

When the light source is placed in the receptacle 646 and turned on, light passes above the upper surface of the stop 652 generally in the direction indicated by arrow 657 and is incident on a bottom surface of the guide 656. If desired, a face may be molded into the bottom surface of the guide 656 and oriented normal (or in another desired orientation) to the direction of the light 657. Through processes of refraction, diffusion and/or internal reflection, light exits the forward-most surfaces of the block 656 and guides 654 generally in the direction indicated by arrow 659. When a standard LED penlight is used as the light source, it has been found that this light, together with other light that illuminates the speculum body 602 and dilator 604, is sufficient to illuminate the procedure site at the front end of the speculum 600. The direction 659 of the exiting light is thus generally aligned with the longitudinal axis of the speculum 600.

Figure 8A:
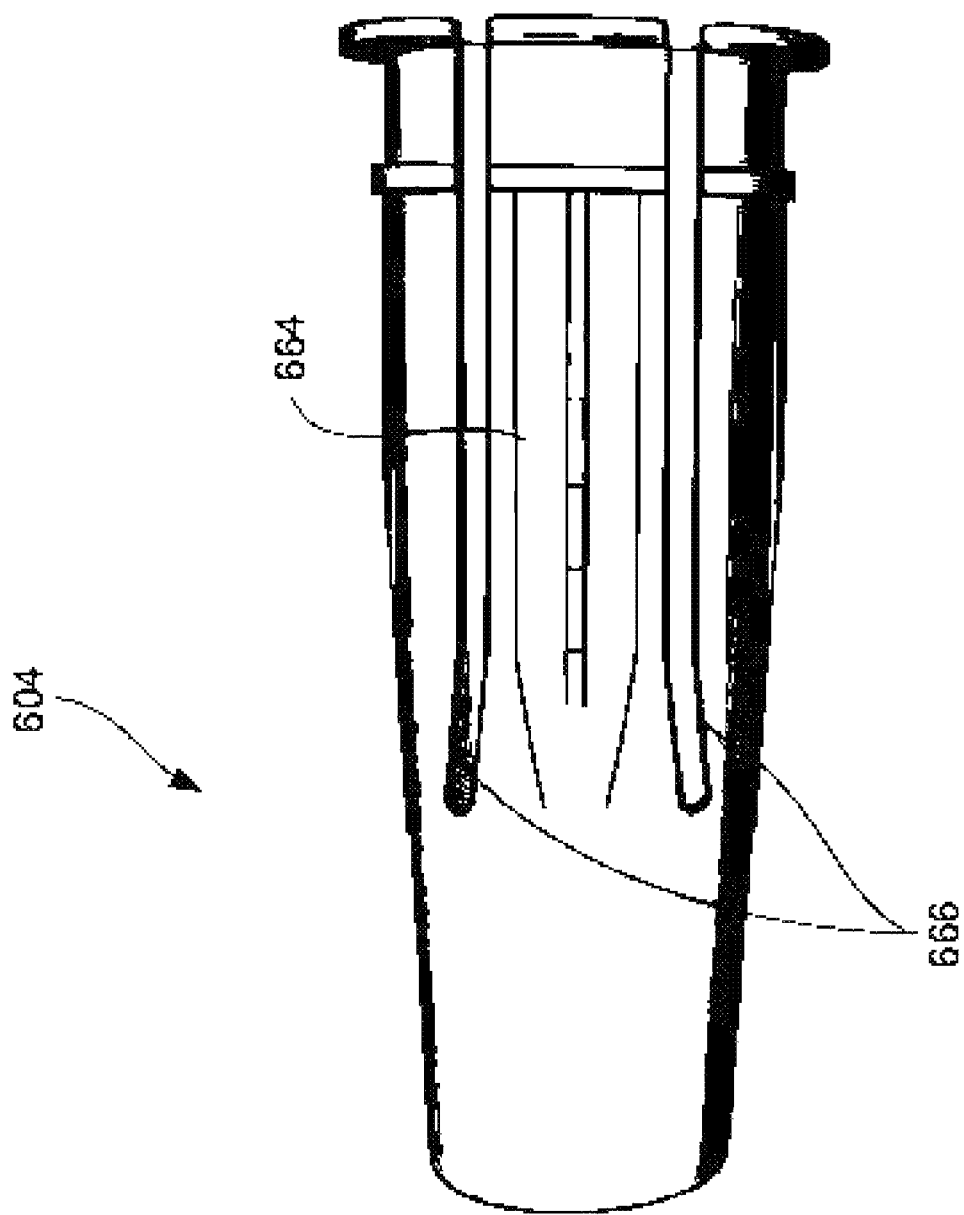
FIG. 8A is a top view of the dilator of the speculum of FIG. 6A.
Figure 8B:
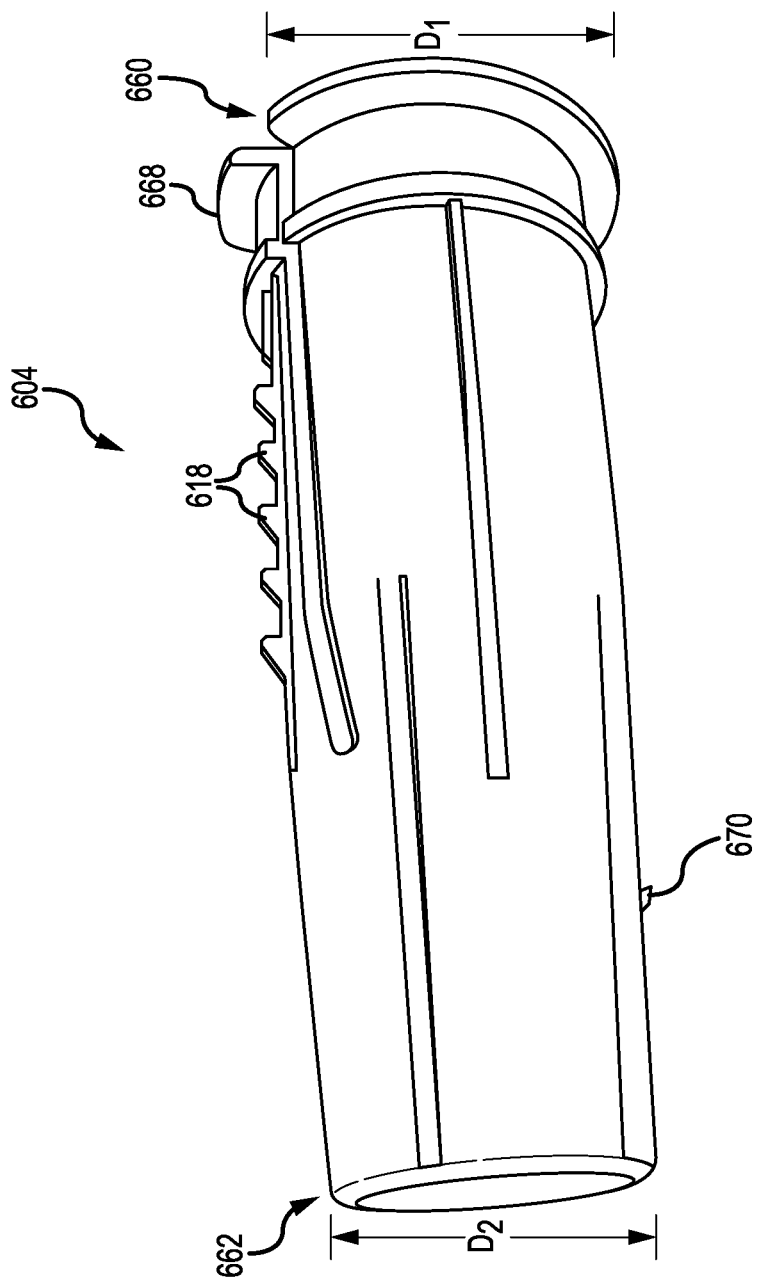
FIG. 8B is a side view of the dilator of the speculum of FIG. 6A.
Figure 8C:
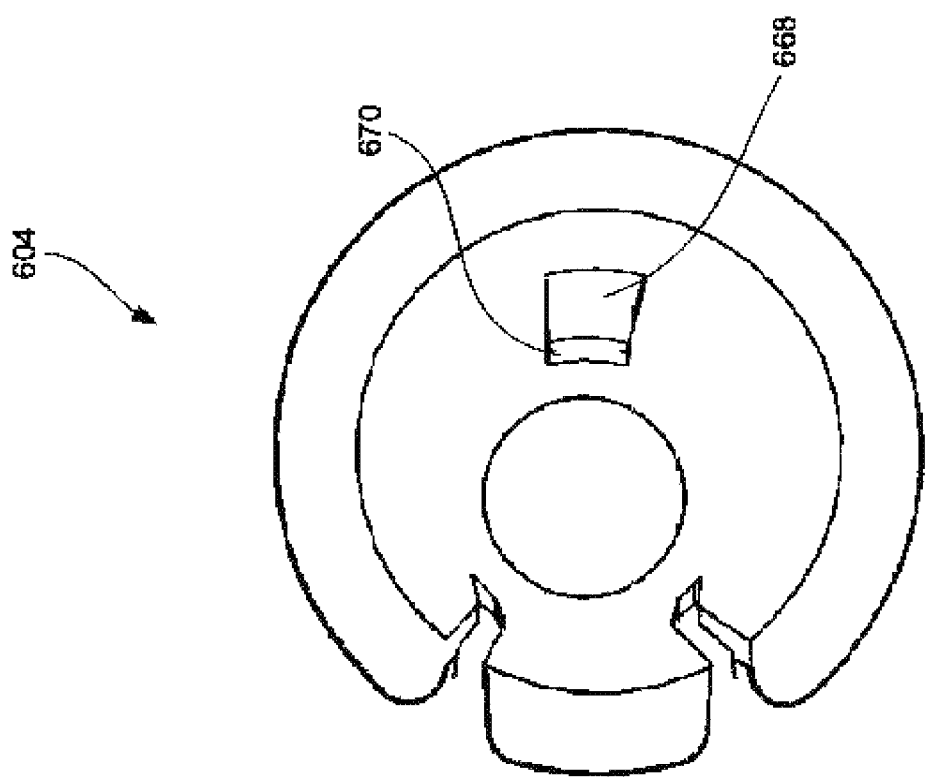
FIG. 8C is a rear view of the dilator of the speculum of FIG. 6A.

FIGS. 8A-8C show various views of the dilator 604. Like the other parts of the speculum 600, the dilator 604 may be formed from molded transparent plastic. As shown, the dilator 604 is slightly tapered from its rear end 662 its forward end 662. This shape better matches the shape of the inner surfaces of the petal assembly 606, facilitates insertion of the dilator 604 into the petal assembly 606 and supports the petal assembly 606 under pressure from the vaginal walls in the dilated configuration. The speculum 600 may be provided in different sizes and shapes in this regard to accommodate different patients, e.g., different ages or different sizes.

As noted above, the dilator 604 includes a thumb flange at the rear end 660 thereof that the user can press to advance the dilator 604. The dilator 604 also includes a collar to limit forward movement of the dilator 604 relative to the speculum body 602. The ratchet teeth 618 are formed on a cantilevered lever defined by slots 666. The cantilevered lever 664 is sufficiently flexible that the lever 664 can be depressed by pressing on the finger grip 668 so as to release the teeth 618 from the recess 660. In this manner, the dilator 604 can be readily withdrawn from the speculum housing 602 and the dilator 604 can be advanced into the speculum body 602 to a desired position without a clicking sound that may be distracting to some patients. The forward ends of the slots 666 flare outwardly slightly from a centerline of the dilator 604 to reduce any structural weakness associated with a single flexion point of the cantilevered portion 664.

The bottom surface of the dilator 604 includes an elongate slot 668. The slot 668 receives the guides 654 (FIG. 7F) and allows for controlled sliding of the dilator 604 in relation to the speculum housing 602. A stop 670 is provided at the forward end of the slot 668 to define the fully retracted position of the dilator 604 in relation to the speculum body 602 and to inhibit inadvertent separation of the dilator 604 from the speculum body 602. The stop 670 is sized, in conjunction with the tapered shape of the dilator 604, to enable separation of the dilator 604 from the speculum body 602 when desired and re-insertion thereof.

The inventive speculum as described above is believed to provide a number of performance advantages in relation to conventional specula. For example, the inventive speculum is believed to provide improved visualization and access to the cervix as well as improved support of the vaginal walls so as to prevent collapsing into the field of view. For example, the multiple petal design and the configuration of the forward petal ends tends to allow for improved access.

The inventive speculum also has potential cost advantages. In this regard, the speculum is of simple and inexpensive construction. In addition, the speculum can be used with an off-the-shelf penlight rather than expensive, custom light sources as sometimes required in connection with conventional specula. Moreover, the configuration of the inventive speculum enables use of the speculum even where custom examination tables are not available.

These potential cost advantages, together with certain other cost-effective measures as described below, allow for the possibility of providing a low cost kit for cervical screening and treatment. Such a kit may be provided in one or more containers that include the principal components needed for cervical screening and treatment. For example, components of the kit deemed to be single use components may be provided in a single sealed container such as a sealed plastic bag. Other components that may be deemed suitable for re-use may be provided in a second container or separately. As a practical matter, this may greatly increase the number of women worldwide who are able to receive screening and treatment and has the potential to dramatically reduce deaths from cervical cancer.

One of the components that may be included in such a kit is a simple set of instructions. An example of what such a set of instructions may look like is shown in FIGS. 9A-9B which also provide a convenient set of illustrations for describing the kit. Referring to FIG. 9A, the first panel of the instructions for screening and treating for cervical cancer shows an example of components that may be included in a kit. The illustrated components include a speculum, surgical gloves, a container of lubricant, a container of a visualization aid, applicators, and a compressed gas container. The use of each of these components will be further explained in the instructions. All of the components shown in the first frame may be included in a single sealed container to provide a relatively inexpensive, self-contained kit for a single procedure. Alternatively, certain components that may be used for more than one procedure, for example, the can of compressed air, the lubricant, and the visualization aid container, may be provided separately such that the kit is defined by multiple kit containers.

As shown in the second panel of the instructions, the user may then snap a penlight (provided as part of the speculum or provided separately as part of the kit) into the handle of the speculum and can turn the penlight on. Panel three instructs the user to apply lubricant to the speculum, e.g., to a latex sleeve extending around the forward end of the petals or directly to the petals. The entire speculum can then be advanced into the patient until resistance is met as shown in panel four. Once the speculum is thus positioned, the user can advance the dilator to dilate the petal assembly to the desired configuration as shown in panel five. Panel six illustrates use of an applicator to apply a visualization agent to the cervix by inserting the applicator through the hollow center of the speculum. Although the instructions indicate that the visualization agent is dilute acetic acid, iodine or other visualization aids are possible.

Referring to FIG. 9B, the instructions proceed with panel seven. Panel seven instructs that, after 45 seconds, the cervix may be observed for any acetowhite lesions. Panel eight provides a depiction of precancerous lesions and cancer of the cervix as well as a normal cervix. Panels nine and ten illustrate a convenient and cost-effective treatment for white lesions. In particular, such lesions may be treated by cryoablation which induces a response in healthy patients that may prevent progression to cancer. In this case, a can of compressed gas is used such as compressed gas cans typically used to remove dust from electronic equipment. Such cans typically include difluoroethane, trifluoroethane or tetrafluoroethene. While these products are marketed as compressed gas containers, the cans generally contain gases that are compressible into liquids. When the can is used in an upright position, high-pressure gas is emitted from the nozzle upon depressing the nozzle and the gas can be precisely directed to the desired location via an elongate tube connected to the nozzle. However, if the can is inverted, a liquid or gas liquid mix may be dispensed. This fluid is dispensed at a very low temperature that, subject to approval or control by a physician where required, may be applied to the lesions for cryoablation treatment.

Thus, panel nine of the instructions directs the user to turn the bottle upside down and spray the tip of the applicator. The applicator can then be inserted through the speculum as shown in panel 10 to apply the cold treatment to the lesions. When treatment is complete, the user can press down on the finger grip of the cantilevered portion of the speculum to withdraw the dilator from the speculum body as shown in panel eleven. The speculum can then be withdrawn from the patient. Panel twelve instructs the user to dispose of the speculum while retaining the penlight for future use.

The foregoing description of the present invention has been presented for the purpose of illustration and description. Furthermore, the description is not intended to limit the invention to the form disclosed herein. Consequently, variations and modifications commensurate with the above teachings, and skill and knowledge of the relevant art are within the scope of the present invention. The embodiments described herein above are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed:

1. A speculum, comprising:
    a handle for gripping by a user;
    a petal assembly, connected to said handle, including a plurality of petals for dilating an introitus of a patient and defining a viewing axis between said petals and extending between a proximate end of said petal assembly adjacent said petal and a distal end of said petal assembly remote from said handle, said petal assembly having a forward portion configured to penetrate into said introitus when said petal assembly is in a retracted configuration and to dilate said introitus when said petal assembly is in an expanded configuration; and
    a dilation actuator including an elongate, hollow dilator, separate from said petal assembly, that can be advanced into and retracted from said forward portion of said petal assembly to respectively dilate and contract said petal assembly, wherein when advanced, the elongate hollow dilator extends beyond a midpoint between the proximate end and distal end of the petal assembly, and wherein said dilation actuator further comprises a ratcheting mechanism, operatively interposed between said elongate, hollow dilator and said petal assembly, defining a number of discrete positions in relation to dilation of said patient's introitus.

2. A speculum as set forth in claim 1, wherein said handle has a longitudinal handle axis disposed at an angle of no more than 75° in relation to said viewing axis.

3. A speculum as set forth in claim 2, wherein said angle is between about 40°-60°.

4. A speculum as set forth in claim 1, wherein said handle includes a grip portion and an offset connector portion extending between said grip portion and said petal assembly, wherein said grip portion is disposed at a nonzero angle in relation to said offset connector portion.

5. A speculum as set forth in claim 1, wherein said dilation actuator includes a thumb surface, disposed rearwardly of said petal assembly adjacent said handle, for manually dilating said petal assembly, said thumb surface being accessible for operation by the user with a thumb of a first hand while said handle is gripped by said first hand.

6. A speculum as set forth in claim 1, wherein said ratcheting mechanism includes a release element disposed at a rearward portion of said ratcheting mechanism.

7. A speculum as set forth in claim 1, wherein said dilator is tapered such that a rearward end of said dilator has a greater cross-sectional dimension than a forward end of said dilator.

8. A speculum, comprising:
    a handle for gripping by a user;
    a petal assembly, connected to said handle, including a plurality of moveable petals for dilating an introitus of a patient and defining a viewing axis between said petals and extending between a proximate end of said petal assembly adjacent said petal and a distal end of said petal assembly remote from said handle, each of said moveable petals being moveable relative to said handle; and
    a dilation actuator including an elongate, hollow dilator, separate from said petal assembly, that can be advanced into and retracted from said petal assembly to respectively dilate and contract said petal assembly, wherein when advanced, the elongate hollow dilator extends beyond a midpoint between the proximate end and distal end of the petal assembly, and wherein said dilation actuator further comprises a ratcheting mechanism, operatively interposed between said elongate, hollow dilator and said petal assembly, defining a number of discrete positions in relation to dilation of said patient's introitus.

9. A speculum as set forth in claim 8, wherein said handle has a longitudinal handle axis disposed at an angle of no more than 75° in relation to said viewing axis.

10. A speculum as set forth in claim 9, wherein said angle is between about 40°-60°.

11. A speculum as set forth in claim 8, wherein said handle includes a grip portion and an offset connector portion extending between said grip portion and said petal assembly, wherein said grip portion is disposed at a nonzero angle in relation to said offset connector portion.

12. A speculum as set forth in claim 8, wherein said ratcheting mechanism includes a release element disposed at a rearward portion of said ratcheting mechanism.

13. A speculum as set forth in claim 8, wherein said dilator is tapered such that a rearward end of said dilator has a greater cross-sectional dimension than a forward end of said dilator.

14. The speculum as set forth in claim 8, wherein said plurality of moveable petals include a first petal moveable in a first direction relative to said handle and a second petal moveable in a second direction, different than said first direction, relative to said handle.

* * * * *